(12) United States Patent
Harada et al.

(10) Patent No.: US 7,253,178 B2
(45) Date of Patent: Aug. 7, 2007

(54) CARBOXYLIC ACIDS

(75) Inventors: Hitoshi Harada, Ibaraki (JP); Masanobu Shinoda, Ibaraki (JP); Richard Clark, Ibaraki (JP); Fumiyoshi Matsuura, Ibaraki (JP); Eita Emori, Ibaraki (JP); Shunji Kasai, Ibaraki (JP); Hideki Yoshitomi, Ibaraki (JP); Kazuto Yamazaki, Ibaraki (JP); Takashi Inoue, Ibaraki (JP); Sadakazu Miyashita, Ibaraki (JP); Taro Hihara, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 692 days.

(21) Appl. No.: 10/469,173

(22) PCT Filed: Mar. 27, 2002

(86) PCT No.: PCT/JP02/03003

§ 371 (c)(1),
(2), (4) Date: Aug. 27, 2003

(87) PCT Pub. No.: WO02/079162

PCT Pub. Date: Oct. 10, 2002

(65) Prior Publication Data

US 2004/0116708 A1    Jun. 17, 2004

(30) Foreign Application Priority Data

Mar. 28, 2001    (JP) ............... 2001-091675

(51) Int. Cl.
A61K 31/435    (2006.01)
A61K 31/44    (2006.01)
C07D 211/72    (2006.01)
C07D 211/70    (2006.01)

(52) U.S. Cl. .............. 514/277; 514/345; 546/301; 546/339

(58) Field of Classification Search ............... 546/301, 546/339; 514/345, 277
See application file for complete search history.

(56) References Cited

FOREIGN PATENT DOCUMENTS

| JP | 9-48771 A | 2/1997 |
|---|---|---|
| WO | WO 99/04815 A1 | 2/1999 |
| WO | WO 99/65897 A1 | 12/1999 |
| WO | WO 00/64876 A1 | 11/2000 |
| WO | WO 00/64888 A1 | 11/2000 |

OTHER PUBLICATIONS

Hcaplus 2006:551484.*
Hcaplus 2006:256663.*
Hulin, Bernard, et al. Current Pharmaceutical Design, vol. 2, No. 1. 1996, pp. 85-102.
Buckle, D. R., et al. Bioorganic & Medicinal Chemistry Letters, vol. 6, No. 17, pp. 2121-2126, 1996.
Bastie, Claire, et al. Journal of Biological Chemistry. vol. 274, No. 31, 1999, pp. 21920-21925.

* cited by examiner

Primary Examiner—Thomas McKenzie
Assistant Examiner—Binta Robinson
(74) Attorney, Agent, or Firm—Birch, Stewart, Kolasch & Birch, LLP

(57) ABSTRACT

The present invention provides a novel carboxylic acid derivative, a salt thereof or a hydrate of them which is useful as an insulin sensitizer, and a medicament comprising the derivative as the effective ingredient. More specifically, it provides a carboxylic acid compound represented by the formula (I), a salt thereof or a hydrate of them.

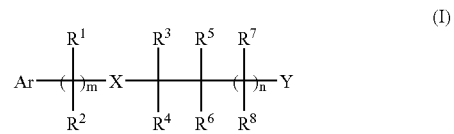

In the formula, Ar represents a 6- to 14-membered aromatic ring group which may have at least one substituent; $R^1$, $R^2$, $R^3$, $R^4$, $R^5$, $R^6$, $R^7$ and $R^8$ are the same as or different from each other and each represents a hydrogen atom, a halogen atom, a hydroxyl group, a $C_{1-6}$ alkyl group or a $C_{1-6}$ alkoxy group; X represents an oxygen atom or a methylene group; Y represents a group represented by the formula (II) or (III):

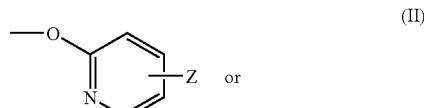

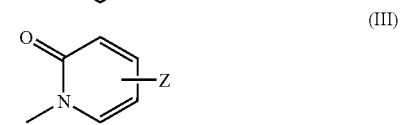

(wherein Z represents a group represented by the formula (IV):

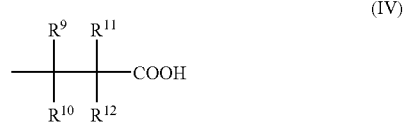

(wherein $R^9$, $R^{10}$, $R^{11}$ and $R^{12}$ are the same as or different from each other and each represents a hydrogen atom, a halogen atom, a hydroxyl group, a $C_{1-6}$ alkyl group or a $C_{1-6}$ alkoxy group)); m is 0 or 1; and n is 0 or 1.

15 Claims, No Drawings

CARBOXYLIC ACIDS

This application is the national phase under 35 U.S.C. § 371 of PCT International Application No. PCT/JP02/03003 which has an International filing date of Mar. 27, 2002, which designated the United States of America.

TECHNICAL FIELD

The present invention relates to a novel carboxylic acid compound useful for prevention or treatment of hyperglycemia and hyperlipemia, a salt thereof, an ester thereof or a hydrate of them, and to a medicament comprising the compound.

PRIOR ART

Diabetes mellitus refers to a durable hyperglycemic condition attributable to the absolute or relative shortage of intrinsic insulin (blood glucose-depressing hormone produced and secreted from Langerhans islet β cells in the pancreas), and in this disease, metabolic abnormalities caused by this condition appear as various morbid states.

Diabetes mellitus is classified roughly into insulin dependent diabetes mellitus (IDDM) that is type 1 diabetes mellitus, for treatment of which insulin administration is absolutely necessary, non insulin dependent diabetes mellitus (NIDDM) that is type 2 diabetes mellitus, and other diabetes mellitus (secondary diabetes mellitus; diabetes mellitus occurs as one symptom of other diseases).

In particular, as life-style is modernized, NIDDM is rapidly increased due to overeating and lack of exercise, thus causing a social problem. While IDDM occurs mainly in infants, NIDDM occurs in middle-aged or elderly persons, to account for the majority of diabetes mellitus in Japan. It is said that NIDDM occurs owing to insulin function-suppressing factors (insulin resistance) such as overeating, lack of exercise, obesity and stress in addition to hereditary factors.

Since excessive intake of calories and obesity resulting from lack of exercise are related to diabetes mellitus as described above, the therapy is based on 3 kinds of therapies, that is, dietary therapy, exercise therapy and chemotherapy.

However, there are not a few cases where dietary therapy and exercise therapy are hard to conduct because of an increase in the number of persons of advanced age in this aging society in recent years.

In chemotherapy of NIDDM, sulfonyl urea (SU) medicines such as tolbutamide, chlorpropamide and tolazamide and biguamide (BG) medicines such as metformin and buformin have been used as oral blood glucose depressants, but the morbid state of NIDDM is characterized by insulin deficiency and insulin resistance, and it cannot be said that the SU medicines stimulating insulin secretion from pancreatic β cells are effective therapeutic medicines for patients with NIDDM condition, where the insulin secretion potential is well but adequate blood glucose control is not achieved in target organs due to insulin resistance, thus permitting hyperglycemia. Further, the BG medicines may permit the onset of lactic acid acidosis, so use of such medicines is limited to a certain extent. Further, these chemicals often caused severe hypoglycemia as a side effect.

To solve these problems, development of chemicals with a new working mechanism is advancing, and thiazolidine derivatives such as Troglitazone, Pioglitazone and Rosiglitazone are called insulin sensitizers, and these chemicals recently attract attention because they can ameliorate insulin resistance (or enhance the action of insulin) and lower blood glucose without promoting secretion of insulin from the pancreas.

It has been revealed that these thiazolidine-type chemicals induce differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953-12956, 1995). By the differentiation of preadipocytes, immature and small adipocytes with less secretion of TNFα, FFA and leptin are increased thus resulting in amelioration of insulin resistance.

Thiazolidine derivatives such as the above Troglitazone, Pioglitazone and Rosiglitazone also act as agonists for PPARγ, to exhibit the effect of ameliorating insulin resistance.

Besides PPARγ, PPAR subtypes such as α, β etc. have been found, any of which regulate expression of genes involved in lipid metabolism. The homology of each subtype among different biological species is higher than the homology of these subtypes in the same species, and with respect to distribution of each subtype in tissues, PPARγ is located substantially in adipose tissues while PPARα occurs mainly in the liver, heart and kidney, and therefore it was considered that each subtype has an independent function. In recent years, it has been revealed that PPARγ mainly mediates lipid anabolism by promoting expression of a group of genes for LPL, acyl-CoA carboxylase, GPDH etc. to convert glucose into lipid and storing the lipid, while PPARα mediates lipid catabolism by regulating expression of a gene group involved in intake of fatty acids into cells and oxidation thereof to decompose lipid.

As thiazolidine derivatives acting as PPARγ and α dual agonists, compounds disclosed in e.g. JP-A 9-48771 are known.

Further, some compounds are known as insulin sensitizers having a carboxylic acid moiety in their structure (Current Pharmaceutical Design, 2, No. 1, pp. 85-102, 1996; Bioorganic & Medicinal Chemistry Letters, 6, No. 17, pp. 2121-2126, 1996).

However, it has been reported that some chemicals acting as PPARγ agonists cause hepatic damage and thus should be carefully used, so chemicals satisfactory in both therapeutic effects and side effects such as toxicity are still not obtained.

Further, compounds having a thiazolidine moiety replaced by a carboxylic acid derivative are merely presented in literatures and not marketed. Further, there is no report showing that such compounds can be used as PPARγ and α dual agonists, and as a matter of course, their γ, α and β(δ) triple agonist action is not known. However, it is also estimated that the toxicity of PPARγ agonists described above is the unique one derived from the thiazolidine moiety, and if a compound exhibiting the above action with a new structure in place of the above structure can be found, the compound can be expected to solve the problem of toxicity, and is thus very useful.

The conventional chemicals are still unsatisfactory in lowering of neutral fat (triglyceride (TG)) related closely to arteriosclerosis.

Further, the action of PPAR β(δ) to induce differentiation of adipocytes is known (J. Biol. Chem., 274, No. 31, pp. 21920-21925), and by this action, cholesterol levels are reported to be lowered (WO9904815), and if a compound having an agonist action for this subtype can be found, this compound can be expected to exhibit a higher activity than that of the conventional insulin sensitizers and to reduce side effects such as hepatic toxicity.

As the PPAR receptor ligands, diaryl acid derivatives are disclosed in WO-A 00/64888 and triaryl derivatives are disclosed in WO-A 00/64876.

As the inhibitors of glycogen synthase kinase 3, pyrimidine or pyrimidine derivatives are disclosed in WO-A 99/65897 (published on Dec. 23, 1999).

From the foregoing aspects, there is demand for development of excellent chemicals.

DISCLOSURE OF THE INVENTION

For the purpose of providing a medicament effective in prevention or treatment of hyperglycemia, which satisfies these various requirements, the present inventors made extensive study and, as a result, they found that a carboxylic acid derivative having a novel structure has an excellent anti-hyperglycemia, anti-hyperlipemia action and inflammatory action, thus completing the present invention.

That is, the present invention relates to 1) a carboxylic acid compound represented by the formula (I):

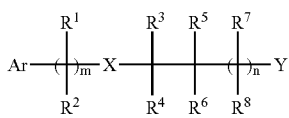

(in the formula, Ar represents a 6- to 14-membered aromatic ring group which may have at least one substituent; $R^1$, $R^2$, $R^3$, $R^4$, $R^5$, $R^6$, $R^7$ and $R^8$ are the same as or different from each other and each represents a hydrogen atom, a hydroxyl group, a halogen atom, a $C_{1-6}$ alkyl group or a $C_{1-6}$ alkoxy group; X represents an oxygen atom or a methylene group; Y represents a group represented by the formula (II) or (III):

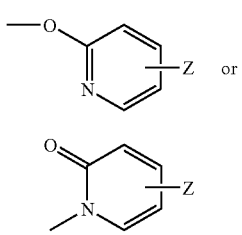

(wherein Z represents a group represented by the formula (IV):

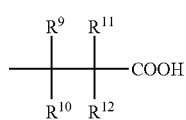

(wherein $R^9$, $R^{10}$, $R^{11}$ and $R^{12}$ are the same as or different from each other and each represents a hydrogen atom, a halogen atom, a hydroxyl group, a $C_{1-6}$ alkyl group or a $C_{1-6}$ alkoxy group)); m is 0 or 1; and n is 0 or 1), a salt thereof or a hydrate of them; 2) the carboxylic acid compound described in the above 1), a salt thereof or a hydrate of them, wherein Y is a group represented by the formula (II):

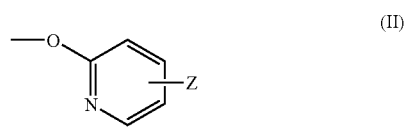

(wherein Z represents a group represented by the formula (IV):

(wherein $R^9$, $R^{10}$, $R^{11}$ and $R^{12}$ are independent of each other and each represents a hydrogen atom, a halogen atom, a hydroxyl group, a $C_{1-6}$ alkyl group or a $C_{1-6}$ alkoxy group)); 3) the carboxylic acid compound described in the above 1), a salt thereof or a hydrate of them, wherein Y represents a group represented by the formula (III):

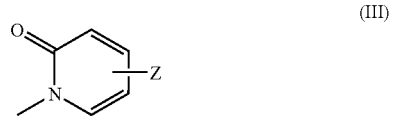

(wherein Z represents a group represented by the formula (IV):

(wherein $R^9$, $R^{10}$, $R^{11}$ and $R^{12}$ are independent of each other and each represents a hydrogen atom, a halogen atom, a hydroxyl group, a $C_{1-6}$ alkyl group or a $C_{1-6}$ alkoxy group)); 4) the carboxylic acid compound described in any one of the above 1) to 3), a salt thereof or a hydrate of them, wherein $R^9$, $R^{10}$ and $R^{11}$ represent a hydrogen atom; and $R^{12}$ represents a $C_{1-6}$ alkoxy group; 5) the carboxylic acid compound described in any one of the above 1) to 4), wherein $R^{12}$ represents an ethoxy group or an isopropoxy group; 6) the carboxylic acid compound described in any one of the above 1) to 5), wherein X represents an oxygen atom; 7) the carboxylic acid compound described in any one of the above 1) to 6), wherein m and n are 0; 8) the carboxylic acid compound described in any one of the above 1) to 7), wherein $R^1$, $R^2$, $R^3$, $R^4$, $R^5$, $R^6$, $R^7$ and $R^8$ represent a hydrogen atom; 9) the carboxylic acid compound described in any one of the above 1) to 8), a salt thereof or a hydrate of them, wherein Ar represents a benzene ring group which may have at least one substituent selected from the group consisting of a halogen atom, a hydroxyl group, a $C_{1-6}$ alkyl group, a $C_{1-6}$ alkoxy group, a $C_{3-6}$ cycloalkyl group and a trifluoromethyl group; 10) a medicament comprising the carboxylic acid compound represented by the following formula (I):

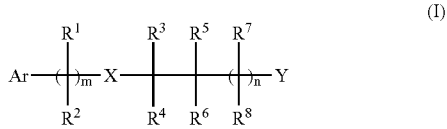

(in the formula, Ar represents a 6- to 14-membered aromatic ring group which may have at least one substituent; $R^1$, $R^2$, $R^3$, $R^4$, $R^5$, $R^6$, $R^7$ and $R^8$ are the same as or different from each other and each represents a hydrogen atom, a halogen atom, a hydroxyl group, a $C_{1-6}$ alkyl group or a $C_{1-6}$ alkoxy group; X represents an oxygen atom or a methylene group; Y represents a group represented by the formula (II) or (III):

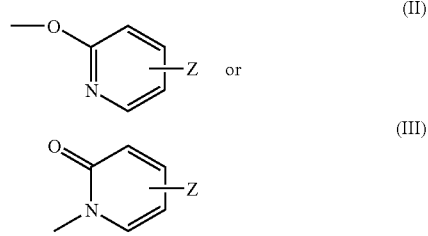

(wherein Z represents a group represented by the formula (IV):

(wherein $R^9$, $R^{10}$ $R^{11}$ and $R^{12}$ are the same as or different from each other and each represents a hydrogen atom, a halogen atom, a hydroxyl group, a $C_{1-6}$ alkyl group or a $C_{1-6}$ alkoxy group)); m is 0 or 1; and n is 0 or 1), a salt thereof or a hydrate of them; 11) the medicament described in the above 10), which is a medicament based on PPAR α and γ dual agonism; 12) the medicament described in the above 10), which is a medicament based on PPAR α, β(δ) and γ triple agonism; 13) the medicament described in any one of the above 10) to 12), which is an insulin sensitizer; 14) the medicament described in any one of the above 10) to 12), which is an agent for preventing or treating diabetes mellitus; 15) the medicament described in any one of the above 10) to 12), which is an agent for preventing or treating syndrome X; 16) the medicament described in any one of the above 10) to 12), which is an agent for preventing or treating an inflammatory disease; 17) the medicament described in 16), in which the inflammatory disease is inflammatory bowel disease; 18) an agent for preventing or treating a disease against which an insulin sensitizing activity is effective, which comprises the compound described in any one of the above 1) to 9) as an effective ingredient; 19) a method for preventing or treating a disease against which an insulin sensitizing action is efficacious, by administering a pharmacologically effective amount of the carboxylic acid compound described in any one of the above 1) to 9), a salt thereof or a hydrate of them to a patient; and 20) use of the carboxylic acid compound described in any one of the above 1) to 9), a salt thereof or a hydrate of them, for producing an agent for preventing or treating a disease against which an insulin sensitizing action is efficacious.

The present invention provides an agent for preventing or treating diabetes mellitus, syndrome X or an inflammatory disease including an inflammatory bowel disease, which comprises the carboxylic acid compound described in any one of the above 1) to 9), a salt thereof or a hydrate of them as an effective ingredient.

Further, the present invention provides a method for preventing or treating diabetes mellitus, syndrome X or an inflammatory disease including an inflammatory bowel disease, by administering a pharmacologically effective amount of the carboxylic acid compound described in any one of the above 1) to 9), a salt thereof or a hydrate of them to a patient.

Furthermore, the present invention provides use of the carboxylic acid compound described in any one of the above 1) to 9), a salt thereof or a hydrate of them, for producing an agent for preventing or treating diabetes mellitus, syndrome X or an inflammatory disease including an inflammatory bowel disease.

In this specification, the structural formulae of the compounds may, for convenience sake, indicate a certain isomer, but the present invention encompasses every possible isomer such as geometric isomer, optical isomer based on asymmetric carbon, stereoisomer and tautomer, which can occur in the structures of the compounds of the present invention, and mixtures of these isomers, and therefore, the compounds of the present invention are not limited by the formulae shown for convenience sake.

The terms used in the specification will be explained below in detail.

The halogen atom as used herein refers to fluorine atom, chlorine atom, bromine atom and iodine atom.

The $C_{1-6}$ alkyl group refers to a linear or branched alkyl group having 1 to 6 carbon atoms. Specific examples include methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group and 1-ethyl-2-methylpropyl group; preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group and i-hexyl group; more preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group and 1,2-dimethylpropyl group; still more preferably methyl group, ethyl group, n-propyl group, i-propyl group, n-butyl group, i-butyl group, sec-butyl group and t-butyl group; and most preferably methyl group, ethyl group, n-propyl group and i-propyl group.

The $C_{1-6}$ alkoxy group refers to a linear or branched alkoxy group having 1 to 6 carbon atoms. Specific examples include a group having an oxygen atom bound to the end of the above-mentioned alkyl group. Specific examples include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group and 1-ethyl-2-methylpropoxy group; preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group and i-hexyloxy group; more preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group and 1,2-dimethylpropoxy group; still more preferably methoxy group, ethoxy group, n-propoxy group, i-propoxy group, n-butoxy group, i-butoxy group, sec-butoxy and t-butoxy; and most preferably methoxy group, ethoxy group, n-propoxy group and i-propoxy group.

With respect to a 6- to 14-membered aromatic ring group which may have at least one substituent, the 6- to 14-membered aromatic ring group refers to a $C_{6-14}$ aromatic hydrocarbon group or a 6- to 14-membered heteroaromatic ring group.

Specific examples of the $C_{6-14}$ aromatic hydrocarbon group include phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cymenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphtyl group, 2-nephtyl group, 1-nephtylmethyl group, 2-naphthylmethyl group, 1-naphthylethyl group, 2-naphthylethyl group, as-indacenyl group, s-indacenyl group and acenaphthylenyl group. Preferably, it is phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-nephthylmethyl group, 2-naphthylmethyl group, 1-naphthylethyl group, 2-naphthylethyl group, as-indacenyl group, s-indacenyl group and acenaphthylenyl group; more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-nephthyl group, 1-nephthylmethyl group and 2-naphthylmethyl group; still more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group and cinnamylidene group; further more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group and phenethyl group; and most preferably phenyl group, o-tolyl group, m-tolyl group, p-tolyl group, 2,3-xylyl group, 2,4-xylyl group, 2,5-xylyl group and benzyl group.

The 6- to 14-membered aromatic heterocyclic ring group includes, for example, pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, chromene, quinoline, isoquinoline, cinnoline, quinazoline, quinoxaline, naphthylidine, phthalazine, purine, pteridine, thienofuran, imidazothiazole, benzofuran, benzothiophene, benzoxazole, benzthiazole, benzthiadiazole, benzimidazole, imidazopyridine, pyrrolopyridine, pyrrolopyrimidine and pyridopyrimidine; preferably pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, chromene, quinoline, isoquinoline, cinnoline, quinazoline, quinoxaline, naphthylidine, phthalazine, purine, pteridine, thienofuran, imidazothiazole, benzofuran, benzothiophene, benzoxazole, benzthiazole, benzthiadiazole, benzimidazole, imidazopyridine, pyrrolopyridine, pyrrolopyrimidine and pyridopyrimidine; more preferably pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, benzoxazole, benzthiazole and benzthiadiazole; still more preferably thiophene, furan, pyrrole, oxazole, isoxazole, thiazole, isothiazole, imidazole, triazole, pyrazole, furazane, thiadiazole, oxadiazole, indole, isoindole and indazole; further more preferably thiophene, furan, pyrrole, oxazole, thiazole, imidazole and indole; and most preferably oxazole and indole.

The expression "may have a substituent" means that it may be substituted by a substituent such as, for example, hydroxyl group; thiol group; nitro group; morpholino group; thiomorpholino group; halogen atom such as fluorine atom, chlorine atom, bromine atom and iodine atom; nitrile group; azide group; formyl group; alkyl group such as methyl group, ethyl group, propyl group, isopropyl group or buthyl group; alkenyl group such as vinyl group, alkyl group or propenyl group; alkynyl group such as ethynyl group, butynyl group or propalgyl group; alkoxy group corresponding to an lower alkyl group, such as methoxy group, ethoxy group, propoxy group or butoxy group; halogenoalkyl group such as fluoromethyl group, difluoromethyl group, trifluoromethyl group and fluoroethyl group; hydroxyalkyl group such as hydroxymethyl group, hydroxyethyl group and hydroxypropyl group; guanidino group; formimidoyl group; acetimidoyl group; carbamoyl group; thiocarbamoyl group; carbamoylalkyl group such as carbamoylmethyl group or carbamoylethyl group; alkylcarbamoyl group such as methylcarbamoyl group or dimethylcarbamoyl group; carbamide group; alkanoyl group such as acetyl group; amino group; alkylamino group such as methylamino group, ethylamino group or isopropylamino group; dialkylamino group such as dimethylamino group, methylethylamino group or diethylamino group; aminoalkyl group such as aminomethyl group, aminoethyl group or aminopropyl group; carboxy group; alkoxycarbonyl group such as methoxycarbonyl group, ethoxycarbonyl group or propoxycarbonyl group; alkoxycarbonylalkyl group such as methoxycarbonylmethyl group, ethoxycarbonylmethyl group, propoxycarbonylmethyl group, methoxycarbonylethyl group, ethoxycarbonylethyl group or propoxycarbonylethyl group; alkyloxyalkyl group such as methyloxymethyl group, methyloxyethyl group, ethyloxymethyl group or ethyloxyethyl group; alkylthioalkyl group such as methylthiomethyl group, methylthioethyl group, ethylthiomethyl group or ethylthioethyl group; aminoalkylaminoalkyl group such as aminomethylaminomethyl group or aminoethylaminomethyl group; alkylcarbonyloxy group such as methylcarbonyloxy group, ethylcarbonyloxy group and isopropylcarbonyloxy group; arylalkoxyalkoxyalkyl group such as benzyloxyethyloxyethyl group; hydroxyalkoxyalkyl group such as hydroxyethyloxymethyl group or hydroxyethyloxyethyl group; arylalkoxyalkyl group such as benzyloxymethyl group, benzyloxyethyl group or benzyloxypropyl group; quaternary ammonio group such as trimethylammonio group, methylethylmethylammonio group or triethylammonio group; cycloalkyl group such as cyclopropyl group, cyclobutyl group, cyclopentyl group, cyclohexyl group or cycloheptyl group; cycloalkenyl group such as cyclopropenyl group, cyclobutenyl group, cyclopentenyl group and cyclohexenyl group; aryl group such as phenyl group, pyridinyl group, thienyl group, furyl group and pyrrolyl group; alkylthio group such as methylthio group, ethylthio group, propylthio group or butylthio group; arylthio group such as phenylthio group, pyridinylthio group, thienylthio group, furylthio group or pyrrolylthio group; aryl lower alkyl group such as benzyl group, trityl group or dimethoxytrityl group; substituted sulfonyl group such as sulfonyl group, mesyl group or p-toluenesulfonyl group; allyloyl group such as benzoyl group; halogenoaryl group such as fluorophenyl group or bromophenyl group; and oxyalkoxy group such as methylenedioxy group.

The expression "may have at least one substituent" means that it may have these groups singly or in any combination. For example, alkyl groups, alkenyl groups, alkynyl groups and alkoxy groups which are substituted with hydroxyl group, thiol group, nitro group, morpholino group, thiomorpholino group, a halogen atom, nitrile group, azide group, formyl group, amino group, an alkylamino group, a dialkylamino group, carbamoyl group, sulfonyl group and the like are also included in the present invention.

In the present invention, the salt includes, but is not limited to, inorganic acid addition salts such as hydrofluorate, hydrochloride, sulfate, nitrate, perchlorate, phosphate, carbonate, bicarbonate, hydrobromate and hydroiodate; organic carboxylic acid addition salts such as acetate, maleate, fumarate, oxalate, lactate, tartrate and trifluoroacetate; organic sulfonic acid addition salts such as methane sulfonate, trifluoromethane sulfonate, ethane sulfonate, hydroxymethane sulfonate, hydroxyethane sulfonate, benzene sulfonate, toluene sulfonate and taurine salt; amine addition salts such as trimethyl amine salt, triethylamine salt, pyridine salt, procaine salt, picoline salt, dicyclohexylamine salt, N,N'-dibenzyl ethylene diamine salt, N-methyl glucamine salt, diethanolamine salt, triethanolamine salt, tris(hydroxymethylamino)methane salt and phenetyl benzyl amine salt; alkali metal addition salts such as sodium salt and potassium salt; alkaline earth metal addition salts such as magnesium salt and calcium salt; and amino acid addition salts such as arginine salt, lysine salt, serine salt, glycine salt, aspartate and glutamate. Preferably, these salts are pharmaceutically acceptable salts.

The pharmaceutically acceptable salts include, but are not limited to, inorganic acid addition salts such as hydrochloride, sulfate, carbonate, bicarbonate, hydrobromate and hydroiodate; organic carboxylic acid addition salts such as acetate, maleate, lactate, tartrate and trifluoroacetate; organic sulfonic acid addition salts such as methanesulfonate, hydroxymethanesulfonate, hydroxyethanesulfonate, benzenesulfonate, toluenesulfonate and taurine salt; amine addition salts such as trimethyl amine salt, triethylamine salt, pyridine salt, procaine salt, picoline salt, dicyclohexylamine salt, N,N'-dibenzyl ethylene diamine salt, N-methyl glucamine salt, diethanolamine salt, triethanolamine salt, tris(hydroxymethylamino)methane salt and phenetyl benzyl amine salt; alkali metal addition salts such as sodium salt and potassium salt; and amino acid addition salts such as arginine salt, lysine salt, serine salt, glycine salt, aspartate and glutamate.

In the present invention, when the carboxylic acid derivatives of the above formula (I) or a salt thereof form solvates, these solvates also fall under the scope of the present invention.

The compounds represented by the formula (I): according to the present invention may be synthesized by conventional methods.

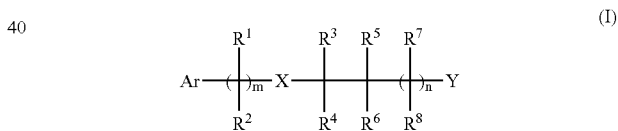

wherein the symbols have the same meanings as defined above.

For example, the compounds can be synthesized by the following methods shown below.

Production Method A

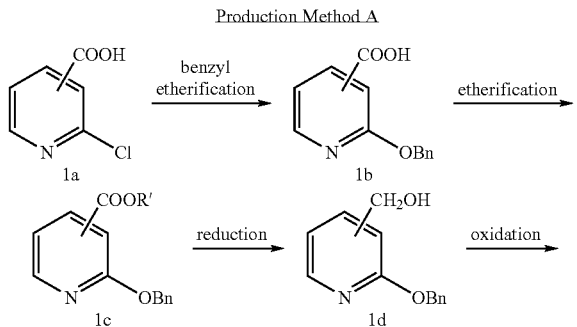

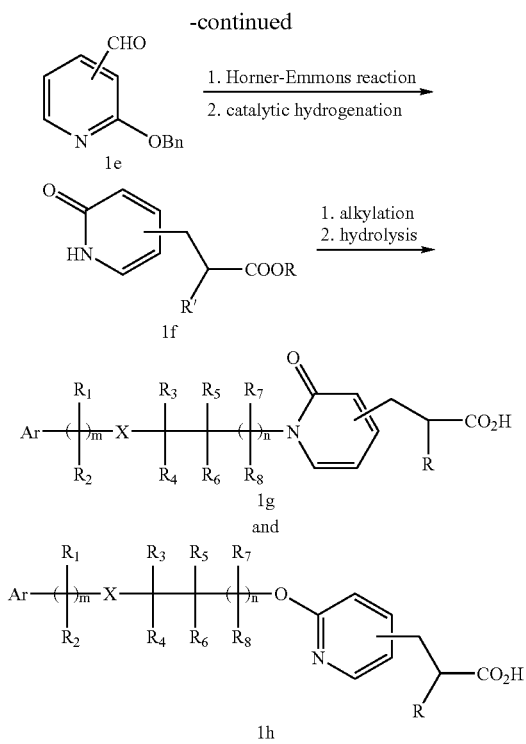

wherein R represents a hydrogen atom, a halogen atom, a hydroxyl group, an alkyl group or an alkoxy group; R' represents an alkyl group; and other symbols have the same meanings as defined above.

The compound of the formula (1b) can be produced by reacting the compound of the formula (1a) with benzyl alcohol in a solvent such as N,N-dimethylformamide, N-methylpyrrolidone, tetrahydrofuran or dimethylsulfoxide in the presence of an base such as sodium hydride, to substitute the chlor group by a benzyloxy group. The reaction temperature is preferably 0 to 100° C.

The compound of the formula (1c) can be produced by reacting the compound of the formula (1b) with an alkyl halide in a solvent such as N,N-dimethylformamide, N-methylpyrrolidone, tetrahydrofuran or dimethylsulfoxide in the presence of an base such as potassium hydrogencarbonate, potassium carbonate or sodium hydrogencarbonate, to esterify the carboxyl group of the compound of the formula (1b). The reaction temperature is preferably 0° C. to room temperature.

The compound of the formula (1d) can be produced by reacting the compound of the formula (1c) with an aluminum hydride compound or a boron hydride compound such as lithium aluminum hydride or sodium tetrahydroborate in a solvent such as diethyl ether or tetrahydrofuran, to reduce the ester group of the compound of the formula (1c) into a hydroxymethyl group. The reaction temperature is preferably 0° C. to room temperature.

The compound of the formula (1e) can be produced by reacting the compound of the formula (1d) with activated manganese dioxide in a solvent such as chloroform, dichloromethane or 1,2-dichloroethane, to oxidize the hydroxymethyl group of the compound of the formula (1d) into a formyl group. The reaction temperature is preferably 0 to 100° C.

The compound of the formula (1f) can be produced by reacting the compound of the formula (1e) with an appropriate phosphonate in a solvent such as N,N-dimethylformamide, N-methylpyrrolidone or tetrahydrofuran, or a mixture thereof in the presence of an base such as sodium hydride, followed by conducting hydrogenation in a solvent such as methanol, ethanol, ethyl acetate or tetrahydrofuran in the presence of a catalyst such as palladium carbon. The reaction temperature is preferably 0° C. to room temperature.

The compounds of the formulae (1g) and (1h) can be produced by reacting the compound of the formula (1f) with an alkyl halide which is a known one or can be produced by Production Method B in a solvent such as N,N-dimethylformamide, N-methylpyrrolidone, tetrahydrofuran, dimethylsulfoxide, acetone or 2-butanone in the presence of an base such as potassium hydrogencarbonate, potassium carbonate, sodium hydrogencarbonate or sodium hydride, to alkylate the oxygen atom or nitrogen atom on the pyridone ring, followed by reacting with a base such as sodium hydroxide in a mixed solvent of an alcohol such as ethanol or methanol and water, to hydrolyze the ester group. The reaction temperature is preferably 0 to 100° C. The resolution of N-alkyl form and O-alkyl form may be performed prior to or after the hydrolysis of the ester group.

Production Method B

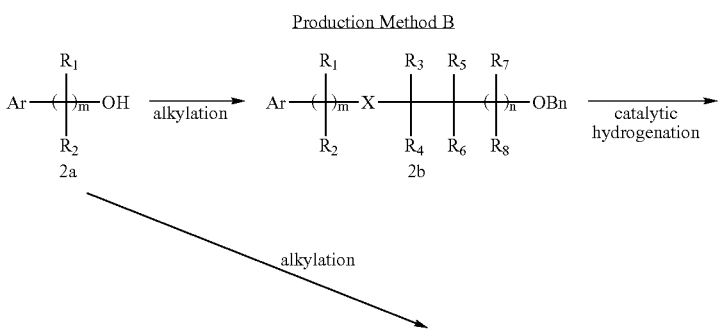

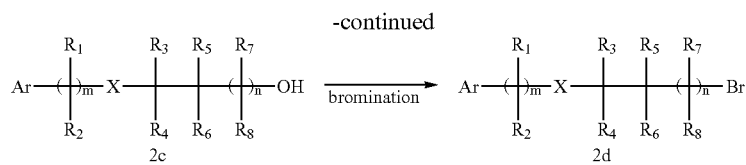

wherein each of the symbols has the same meaning as defined above; and Bn represents a benzyl group.

The compound of the formula (2b) can be produced by reacting the compound of the formula (2a) with an alkyl halide such as benzyl 2-bromoethyl ether in a solvent such as N,N-dimethylformamide, N-methylpyrrolidone, tetrahydrofuran, dimethylsulfoxide, acetone or 2-butanone in the presence of an base such as potassium hydrogencarbonate, potassium carbonate, sodium hydrogencarbonate or sodium hydride, to alkylate the oxygen atom of the compound of the formula (2a). The reaction temperature is preferably 0 to 100° C.

The compound of the formula (2c) can be produced by conducting hydrogenation of the compound of the formula (2b) in a solvent such as methanol, ethanol, ethyl acetate or tetrahydrofuran in the presence of a catalyst such as palladium carbon or palladium hydroxide. The reaction temperature is preferably 0° C. to room temperature.

The compound of the formula (2d) can be produced by reacting the compound of the formula (2c) with phosphorous tribromide or the like in a solvent such as 1,2-dimethoxyethane, to brominate the hydroxyl group of the compound of the formula (2c). The reaction temperature is preferably 0° C. to room temperature.

The compound of the formula (2d) can be produced by reacting the compound of the formula (2a) with an alkyl halide such as 1,2-dibromoethane or 1,3-dibromopropane in a solvent such as N,N-dimethylformamide, N-methylpyrrolidone, tetrahydrofuran, dimethylsulfoxide, acetone or 2-butanone in the presence of an base such as potassium hydrogencarbonate, potassium carbonate, sodium hydrogencarbonate, sodium hydride, to alkylate the oxygen atom of the compound of the formula (2a). The reaction temperature is preferably 0 to 100° C.

As described above, the solvent usable in the present invention is not particularly limited, and may be any solvent ordinarily used in organic synthesis and not inhibiting the reaction. Specific examples include mixed solvents in any ratio of one or more solvents such as lower alcohols such as methanol, ethanol, propanol and butanol; polyalcohols such as ethylene glycol and glycerin; ketones such as acetone, methyl ethyl ketone, diethyl ketone and cyclohexanone; ethers such as diethyl ether, isopropyl ether, tetrahydrofuran, dioxane, 2-methoxyethanol and 1,2-dimetehoxyethane; nitriles such as acetonitrile and propionitrile; esters such as methyl acetate, ethyl acetate, isopropyl acetate, butyl acetate and diethyl phthalate; halogenated hydrocarbons such as dichloromethane, chloroform, carbon tetrachloride, 1,2-dichloroethane, trichloroethylene and tetrachloroethylene; aromatics such as benzene, toluene, xylene, monochlorobenzene, nitrobenzene, indene, pyridine, quinoline, collidine and phenol; hydrocarbons such as pentane, cyclohexane, hexane, heptane, octane, isooctane, petroleum benzine and petroleum ether; amines such as ethanolamine, diethylamine, triethylamine, pyrrolidine, piperidine, piperazine, morpholine, aniline, dimethylaniline, benzylamine and toluidine; amides such as formamide, N-methylpyrrolidone, N,N-dimethylimidazolone, N,N-dimethylacetamide and N,N-dimethylformamide; phosphoric acid amides such as hexamethylphosphoric acid triamide and hexamethylphosphorous acid triamide; water; and other generally used solvents.

As described above, the base usable in the present invention is not particularly limited, and may be any base usually known as a base in organic synthesis and not inhibiting the reaction. Specific examples include sodium carbonate, sodium hydrogencarbonate, potassium carbonate, sodium hydride, potassium hydride, t-butoxy potassium, pyridine, dimethylaminopyridine, trimethylamine, triethylamine, N,N-diisopropylethylamine, N-methylmorpholine, N-methylpyrrolidine, N-methylpiperidine, N,N-dimethylaniline, 1,8-diazabicyclo[5,4,0]undec-7-ene (DBU), pyridine, 4-dimethylaminopyridine, picoline, lutidine, quinoline, isoquinoline, sodium hydroxide, potassium hydroxide, lithium hydroxide, butyl lithium, and sodium or potassium alcolates such as sodium methylate, potassium methylate and sodium ethylate.

After the reaction is completed, the product can be purified if necessary by usual treatment methods such as column chromatography on silica gel or adsorption resin, or by re-crystallization from a suitable solvent.

The medicament according to the present invention improves insulin resistance by the agonism of PPAR as described above, and the present invention can be applied not only as an insulin sensitizer but also as various medicaments based on PPAR (α, β(δ), γ) agonism (based on e.g. PPAR α and γ dual agonism or on PPAR α, β(δ) and γ triple agonism).

For example, the relationship of PPAR not only with insulin resistance but also with blood lipid or inflammatory diseases is known (Current Opinion in Lipidol. 10:245-257, 1999; Jiang, C., et al., PPAR-gamma agonists inhibit production of monocyte inflammatory cytokines, Nature 391: 82-86 (1998); Jackson, S. M., et al., Peroxisome proliferator-activated receptor activators target human endothelial cells to inhibit leukocyte-endothelial cell interaction., Arterioscler. Thromb. Vasc. Biol. 19: 2094-2104 (1999); Su, C. G., et al., A novel therapy for colitis utilizing PPAR-gamma ligands to inhibit the epithelial inflammatory response., J Clin Invest 1999 August;104(4):383-9; Ricote, M., et al., The peroxisome proliferator-activated receptor-gamma is a negative regulator of macrophage activation., Nature 1998 Jan. 1;391(6662):79-82), and the medicament of the present invention can be applied to diseases against which it is reported to be effective in these literatures.

The dose of the pharmaceutical preparation of the present invention, though being varied depending on the severeness of symptom, age, sex, body weight, administration form and the type of disease, is usually 100 μg to 10 g/day/adult, and this dose is administered in one or divided portions.

The administration form of the medicament of the present invention is not particularly limited, and it can be administered orally or parenterally by an ordinarily used method.

For manufacturing of the medicament, ordinarily used fillers, binders, lubricants, coloring agents, flavoring agents and if necessary stabilizers, emulsifiers, absorption promoters, surfactants etc. can be used, and ingredients used generally as starting materials for medicament are compounded in a usual manner.

These ingredients include e.g. animal and vegetable oils (such as soybean oil, tallow and synthetic glyceride), hydrocarbons (such as liquid paraffin, squalene and solid paraffin), ester oils (such as octyldodecyl myristate and isopropyl myristate), higher alcohols (such as cetostearyl alcohol and behenyl alcohol), silicon resin, silicon oil, surfactants (polyoxyethylene fatty ester, sorbitan fatty ester, glycerin fatty ester, polyoxyethylene sorbitan fatty ester, polyoxyethylene hardened castor oil and polyoxyethylene-polyoxypropylene block copolymer), water-soluble polymers (such as hydroethyl cellulose, polyacrylic acid, carboxyvinyl polymer, polyethylene glycol, polyvinyl pyrrolidone and methyl cellulose), alcohols (such as ethanol and isopropanol), polyvalent alcohols (such as glycerin, propylene glycol, dipropylene glycol and sorbitol), sugars (such as glucose and sucrose), inorganic powder (such as silicic anhydride, aluminum magnesium silicate and aluminum silicate), and pure water. For pH adjustment, it is possible to use inorganic acids (such as hydrochloric acid and phosphoric acid), alkali metal salt of inorganic acid (such as sodium phosphate), inorganic bases (such as sodium hydroxide), organic acids (such as lower fatty acids, citric acid and lactic acid), alkali metal salts of organic acid (such as sodium citrate and sodium lactate) and organic bases (such as arginine and ethanolamine). If necessary, preservatives, antioxidants etc. can be added.

Hereinafter, pharmacological experiment examples are shown to show the usefulness of this invention.

Experiment Example 1

Measurement of Blood Glucose Reduction, Blood Triglyceride Reduction and Blood Non-esterified Fatty Acids A chemical suspended in 0.5% methyl cellulose was orally administered via a sonde into male db/db mice (Nippon Charles River, Yokohama, JP) once a day (30 mg/kg/day. Before treatment and after 4 and 9 days treatment, blood was collected from tail vein after the mice were fasted for 1 hour, respectively. On Day 10, an oral glucose loading test was conducted; in this test, the mice were fasted overnight from the previous day, and in the next morning, 2 g/kg glucose was given to the mice. Plasma glucose, triglycerides (TG), non-esterified fatty acids (NEFA) were measured by using commercial kits, that is, Glucose C-II Test Wako (trade name) (Wako Pure Chemical Industries, Ltd., Tokyo), Deteminer L TG II (trade name) (Kyowa Medex, Tokyo) and NEFA C-Test Wako (Wako Pure Chemical Industries, Ltd., Tokyo), respectively. The compounds of the present invention show excellent rates of blood glucose reduction, blood tridglyceride reduction and blood non-esterified fatty acids reduction.

Experiment Example 2

Measurement of Transcriptional Activity

A GAL4-PPAR LBD chimera expression vector was constructed by ligating human PPAR 167-468 (PPARα), 138-440 (NUC-1) and 174-475 (PPARγ) amino acid regions (LBD: Ligand Binding Domain) to a yeast transcriptional factor GAL4 1-147 amino acid region. As the reporter gene, PLAP (Placental Alkaline Phosphatase) was used, and this was ligated downstream of a TK promoter containing a 5-copy GAL4 DNA binding element to construct a vector. As host cells, CV-1 (ATCC CCL-70) was used. That is, CV-1 cells were spread at a density of $5 \times 10^5$ cells on a 35-mm dish and cultured in 10% FCS/DMEM for 24 hours, and using FuGENE 6 transfection reagent, the cells were co-transfected with the GAL4-PPAR LBD expression vector and GAL4 DBD-TK-PLAP expression vector. 24 hours after this transfection, the cells were spread again on a 96-well plate at a density of $1 \times 10^4$/well and further cultured for 24 hours. After 24 hours, the medium was exchanged with DMEM containing 10% FCS, which was previously treated at 65° C. for inactivating intrinsic alkaline phosphatase, and a test compound was added at an arbitrary concentration. The transcriptional activity was determined in terms of PLAP activity secreted 24 hours after addition of the compound, to calculate $EC_{50}$. The PLAP activity was determined after adding 50 μl assay buffer and 50 μl chemoluminescence substrate to 10 μl culture supernatant and incubating the mixture at room temperature for 1 hour. The transcriptional activities for PPAR, PPARβ(δ) and PPARγ are shown respectively in Table 1.

TABLE 1

| | Transcriptional activities $EC_{50}$ (Unit: nM) | | |
|---|---|---|---|
| | PPAR α | PPAR β | PPAR γ |
| Example 1 | 5.6 | 1410 | 68.5 |
| Example 19 | 4.9 | 338.6 | 64.1 |
| Example 25 | 2.7 | 1577 | 76.3 |

As described above, the compounds of the present invention have an excellent blood glucose- and blood lipid-ameliorating action and are very useful as anti-diabetes agents, anti-hyperlipemia agents and insulin sensitizers.

Example 3

Anti-inflammatory Effect

Experimental colitis was induced in female ICR mice (10 mice/group, Charles River Japan, Yokohama) by giving 4% dextran sulfate sodium in drinking water for 5 days. After 8 days, the mice were grouped into sections from "0" (normal) to "4" (severe) based on change in diarrhea, hematochezia and weight loss as described by Cooper HS et al., (Laboratory Invest (69), pp. 238-249, 1993) and the average of the values was used as the Disease Activity Index for colitis. Each test compound was suspended in a 0.5% methylcellulose solution and administered to the mice orally once a day via a sonde from the day when the induction of colitis was initiated. The compounds of the present invention have an excellent anti-inflammatory effect.

EXAMPLES

Examples below will illustrate the present invention more in detail and more specifically. However, the invention should not be limited by these Examples.

Production Example 1-a)

2-(2,4-Dichlorophenoxy)-1-ethanol

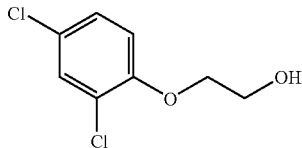

To a solution of 2,4-dichlorophenoxy acetic acid (15.0 g) in tetrahydrofuran (300 mL) was added dropwise 1.0M borane-tetrahydrofuran complex/tetrahydrofuran solution (96 mL) under ice-cooling over 1.5 hours. The reaction solution was stirred at room temperature for 22 hours. After the reaction solution was concentrated, the residue was diluted with saturated aqueous ammonium chloride solution and ethyl acetate. The organic layer was washed with saturated ammonium chloride, saturated aqueous sodium hydrogencarbonate solution (×2) and saturated ammonium chloride, dried over anhydrous sodium sulfate and then concentrated, to give the title compound as a colorless oil (14 g).

$^1$H-NMR(CDCl$_3$)δ: 2.21 (d, J=6.4 Hz, 1H) 3.99 (dt, J=4.4, 6.4 Hz, 2H) 4.12 (t, J=4.4 Hz, 2H) 6.87 (d, J=8.8 Hz, 1H) 7.20 (dd, J=2.4, 8.8 Hz, 1H) 7.37 (d, J=2.4 Hz, 1H)

Production Example 1-b)

1-(2-Bromoethoxy)-2,4-dichlorobenzene

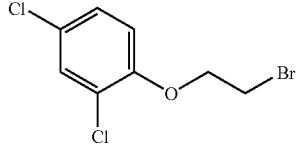

To a solution of 2-(2,4-dichlorophenoxy)-1-ethanol (10.0 g) in 1,2-dimethoxyethane (200 mL) was added dropwise a solution of phosphorous tribromide (14 g) in 1,2-dimethoxyethane (20 mL) under ice-cooling. The reaction solution was stirred at room temperature for 20 hours. After the reaction solution was concentrated, the residue was diluted with water and ethyl acetate. When saturated aqueous sodium hydrogencarbonate solution was added to the organic layer, an emulsion was formed, which was filtered through Celite. The filtrate was diluted with diethyl ether and saturated aqueous ammonium chloride solution. The organic layer was dried over anhydrous magnesium sulfate and then concentrated. The residue was purified by silica gel column chromatography to yield the title compound as a pale yellow oil (6.15 g).

$^1$H-NMR(CDCl$_3$)δ: 3.67 (t, J=6.4 Hz, 2H) 4.32 (t, J=6.4 Hz, 2H) 6.87 (d, J=8.8 Hz, 1H) 7.19 (dd, J=2.6, 8.8 Hz, 1H) 7.39 (d, J=2.6 Hz, 1H)

Production Example 2

1-(2-Bromoethoxy)-4-(trifluoromethyl)benzene

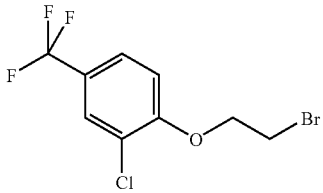

A suspension of 4-hydroxybenzotrifluoride (5.0 g), 1,2-dibromoethane (17.4 g) and potassium carbonate (2.6 g) in acetone (100 mL) was heated under reflux for 3 days. The reaction solution was diluted with water and ethyl acetate. The organic layer was washed with saturated aqueous sodium hydrogencarbonate solution and saturated ammonium chloride (×2), dried over anhydrous sodium sulfate and concentrated. The residue was purified by silica gel column chromatography to give the title compound as a colorless oil (1.78 g).

$^1$H-NMR(CDCl$_3$)δ: 3.66 (t, J=6.4 Hz, 2H) 4.34 (t, J=6.4 Hz, 2H) 6.98 (d, J=8.4 Hz, 2H) 7.56 (d, J=8.4 Hz, 2H)

Production Example 3-a)

1-[2-(Benzyloxy)ethoxy]-4-cyclohexylbenzene

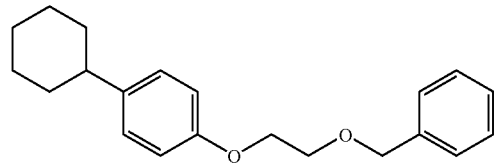

A suspension of 4-cyclohexylphenol (2.5 g), benzyl 2-bromoethyl ether (3.0 g) and potassium carbonate (2.4 g) in N,N-dimethylformamide (50 mL) was stirred at 60° C. for 23 hours. The reaction solution was diluted with water and ethyl acetate. The organic layer was washed with saturated aqueous potassium carbonate solution and saturated ammonium chloride (×2), dried over anhydrous sodium sulfate and concentrated. The residue was purified by silica gel column chromatography to give the title compound as a colorless oil (3.9 g).

$^1$H-NMR(CDCl$_3$)δ: 1.20-1.44 (m, 5H) 1.70-1.90 (m, 5H) 2.39-2.48 (m, 1H) 3.82 (t, J=4.8 Hz, 2H) 4.13 (t, J=4.8 Hz, 2H) 4.63 (s, 2H) 6.83-6.88 (m, 2H) 7.09-7.14 (m, 2H) 7.26-7.38 (m, 5H)

Production Example 3-b)

2-(4-Cyclohexylphenoxy)-1-ethanol

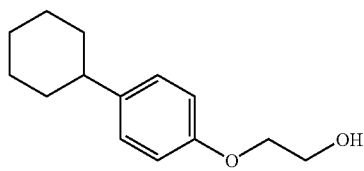

1-[2-(Benzyloxy)ethoxy]-4-cyclohexylbenzene (3.2 g) was dissolved in ethanol (100 mL). The resulting solution was added with 20% palladium hydroxide (300 mg) and then stirred in a hydrogen atmosphere at room temperature for 25 hours. The catalyst was filtered off, and washed with ethyl acetate. The filtrate was evaporated, and the residue was azeotroped with toluene (×2) to give the title compound as a colorless solid (2.34 g).

$^{1}$H-NMR(CDCl$_{3}$)δ: 1.16-1.45 (m, 5H) 1.70-1.90 (m, 5H) 2.12 (br s, 1H) 2.40-2.49 (m, 1H) 3.94 (t, J=4.4 Hz, 2H) 4.06 (t, J=4.4 Hz, 2H) 6.83-6.87 (m, 2H) 7.10-7.15 (m, 2H)

Production Example 3-c)

1-(2-Bromoethoxy)-4-cyclohexylbenzene

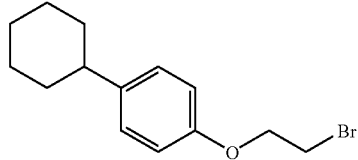

The compound of Production Example 3-c) was synthesized in the same manner as in Production Example 1-b).

$^{1}$H-NMR(CDCl$_{3}$)δ: 1.17-1.44 (m, 5H) 1.70-1.90 (m, 5H) 2.40-2.50 (m, 1H) 3.62 (t, J=6.4 Hz, 2H) 4.27 (t, J=6.4 Hz, 2H) 6.82-6.87 (m, 2H) 7.11-7.15 (m, 2H)

Production Example 4-a)

1-[2-(Benzyloxy)ethoxy]-4-cyclopentylbenzene

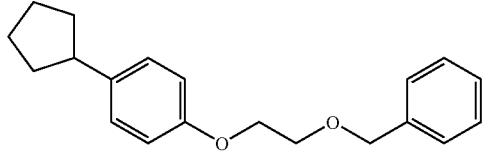

The compound of Production Example 4-a) was synthesized in the same manner as in Production Example 3-a).

$^{1}$H-NMR(CDCl$_{3}$)δ: 0.98-1.10 (m, 2H) 1.60-1.73 (m, 2H) 1.73-1.84 (m, 2H) 1.98-2.08 (m, 2H) 2.89-2.97 (m, 1H) 3.82 (t, J=5.0 Hz, 2H) 4.13 (t, J=5.0 Hz, 2H) 4.63 (s, 2H) 6.83-6.88 (m, 2H) 7.12-7.17 (m, 2H) 7.26-7.38 (m, 5H)

Production Example 4-b)

2-(4-Cyclopentylphenoxy)-1-ethanol

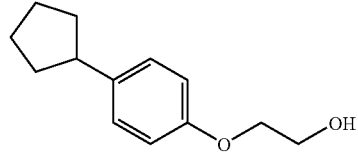

The compound of Production Example 4-b) was synthesized in the same manner as in Production Example 3-b).

$^{1}$H-NMR(CDCl$_{3}$)δ: 1.48-1.84 (m, 6H) 2.00-2.10 (m, 3H) 2.90-2.99 (m, 1H) 3.92-3.98 (m, 2H) 4.07 (t, J=5.0 Hz, 2H) 6.83-6.87 (m, 2H) 7.14-7.19 (m, 2H)

Production Example 4-c)

1-(2-Bromoethoxy)-4-cyclopentylbenzene

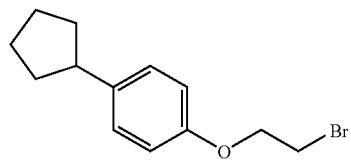

The compound of Production Example 4-c) was synthesized in the same manner as in Production Example 1-b).

$^{1}$H-NMR(CDCl$_{3}$)δ: 1.48-1.84 (m, 6H) 2.00-2.08 (m, 2H) 2.90-2.98 (m, 1H) 3.63 (t, J=6.4 Hz, 2H) 4.27 (t, J=6.4 Hz, 2H) 6.83-6.86 (m, 2H) 7.14-7.18 (m, 2H)

Production Example 5-a)

1-[2-(Benzyloxy)ethoxy]-4-(tert-butyl)benzene

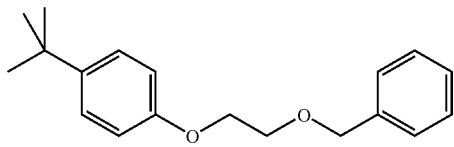

The compound of Production Example 5-a) was synthesized in the same manner as in Production Example 3-a).

$^{1}$H-NMR(CDCl$_{3}$)δ: 1.30 (s, 9H) 3.82 (t, J=5.0 Hz, 2H) 4.14 (t, J=5.0 Hz, 2H) 4.63 (s, 2H) 6.84-6.89 (m, 2H) 7.26-7.38 (m, 7H)

Production Example 5-b)

2-[4-(tert-Butyl)phenoxy]-1-ethanol

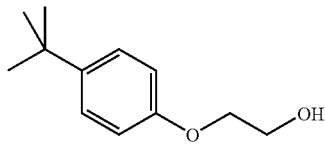

The compound of Production Example 5-b) was synthesized in the same manner as in Production Example 3-b).

$^{1}$H-NMR(CDCl$_{3}$)δ: 1.30 (s, 9H) 2.04 (br, 1H) 3.95 (t, J=4.4 Hz, 2H) 4.07 (t, J=4.4 Hz, 2H) 6.84-6.89 (m, 2H) 7.29-7.33 (m, 2H)

Production Example 5-c)

1-(2-Bromoethoxy)-4-(tert-butyl)benzene

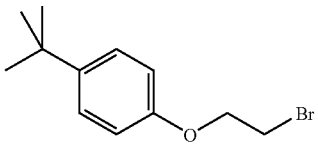

The compound of Production Example 5-c) was synthesized in the same manner as in Production Example 1-b).
$^1$H-NMR(CDCl$_3$)δ: 1.31 (s, 9H) 3.64 (t, J=6.4 Hz, 2H) 4.29 (t, J=6.4 Hz, 2H) 6.84-6.89 (m, 2H) 7.30-7.34 (m, 2H)

Production Example 6-a)

1-[2-(Benzyloxy)ethoxy]-4-isopropylbenzene

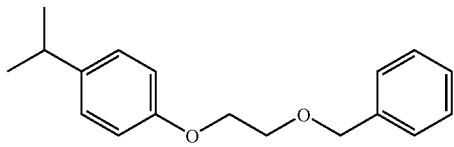

The compound of Production Example 6-a) was synthesized in the same manner as in Production Example 3-a).
$^1$H-NMR(CDCl$_3$)δ: 1.22 (d, J=6.8 Hz, 6H) 2.86 (sept, J=6.8 Hz, 1H) 3.82 (t, J=4.8 Hz, 2H) 4.13 (t, J=4.8 Hz, 2H) 4.63 (s, 2H) 6.84-6.88 (m, 2H) 7.11-7.16 (m, 2H) 7.26-7.39 (m, 5H)

Production Example 6-b)

2-(4-Isopropylphenoxy)-1-ethanol

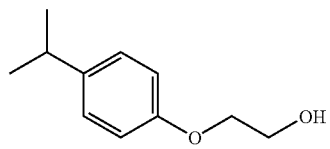

The compound of Production Example 6-b) was synthesized in the same manner as in Production Example 3-b).
$^1$H-NMR(CDCl$_3$)δ: 1.22 (d, J=6.8 Hz, 6H) 2.06 (br s, 1H) 2.87 (sept, J=6.8 Hz, 1H) 3.92-3.98 (m, 2H) 4.07 (t, J=4.8 Hz, 2H) 6.84-6.88 (m, 2H) 7.13-7.17 (m, 2H)

Production Example 6-c)

1-(2-Bromoethoxy)-4-isopropylbenzene

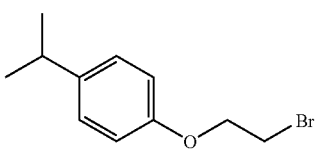

The compound of Production Example 6-c) was synthesized in the same manner as in Production Example 1-b).

$^1$H-NMR(CDCl$_3$)δ: 1.23 (d, J=6.8 Hz, 6H) 2.87 (sept, J=6.8 Hz, 1H) 3.63 (t, J=6.4 Hz, 2H) 4.27 (t, J=6.4 Hz, 2H) 6.83-6.88 (m, 2H) 7.13-7.17 (m, 2H)

Production Example 7

1-(3-Bromopropoxy)-2,4-dichlorobenzene

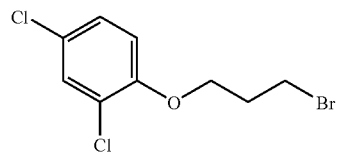

The compound of Production Example 7 was synthesized in the same manner as in Production Example 2.
$^1$H-NMR(CDCl$_3$)δ: 2.36 (quint, J=6.0 Hz, 2H) 3.66 (t, J=6.0 Hz, 2H) 4.15 (t, J=6.0 Hz, 2H) 6.88 (d, J=8.8 Hz, 1H) 7.17-7.21 (m, 1H) 7.36-7.38 (m, 1H)

Production Example 8

1-(3-Bromopropoxy)-4-isopropylbenzene

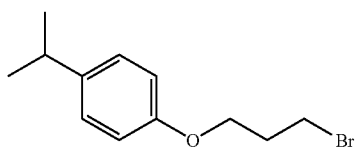

The compound of Production Example 8 was synthesized in the same manner as in Production Example 2.
$^1$H-NMR(CDCl$_3$)δ: 1.22 (d, J=6.8 Hz, 6H) 2.31 (quint, J=6.0 Hz, 2H) 2.86 (sept, J=6.8 Hz, 1H) 3.60 (t, J=6.0 Hz, 2H) 4.08 (t, J=6.0 Hz, 2H) 6.83-6.87 (m, 2H) 7.12-7.17 (m, 2H)

Production Example 9

1-(3-Bromopropoxy)-4-cyclohexylbenzene

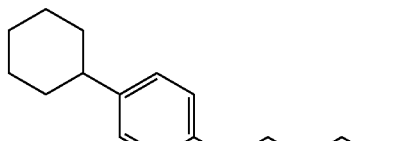

The compound of Production Example 9 was synthesized in the same manner as in Production Example 2.
$^1$H-NMR(CDCl$_3$)δ: 1.18-1.29 (m, 1H) 1.31-1.44 (m, 4H) 1.70-1.90 (m, 5H) 2.40-2.48 (m, 1H) 2.30 (quint, J=6.0 Hz, 2H) 3.60 (t, J=6.0 Hz, 2H) 4.08 (t, J=6.0 Hz, 2H) 6.81-6.86 (m, 2H) 7.09-7.15 (m, 2H)

Production Example 10-a)

2-(Benzyloxy)isonicotinic acid

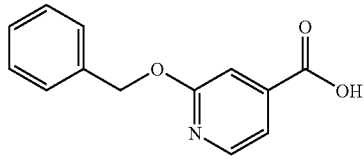

To a suspension of sodium hydride (14.0 g) in N,N-dimethylformamide (250 mL) was added dropwise benzyl alcohol (20.6 g) under ice-cooling over 30 minutes and then added 2-chloroisonicotinic acid (25.0 g) thereto. The reaction solution was stirred at room temperature for 2 hours and then at 70° C. for 13 hours. The reaction solution was allowed to cool to room temperature, diluted with about decuple volumes of water, and then adjusted to pH 5 with 5N hydrochloric acid. The resulting crystals were collected by filtration and then washed with water and hexane to give the title compound as a colorless solid (12.6 g).

$^1$H-NMR(DMSO-d$_6$)δ: 5.40 (s, 2H) 7.30-7.48 (m, 7H) 8.35 (dd, J=0.4, 5.2 Hz, 1H)

Production Example 10-b)

Methyl 2-(benzyloxy)isonicotinate

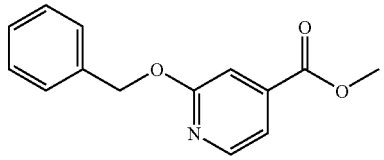

To a suspension of 2-(benzyloxy)isonicotinic acid (12.6 g) and potassium hydrogencarbonate (8.3 g) in N,N-dimethylformamide (180 mL) was added dropwise iodomethane (4.8 mL) under ice-cooling, and then stirred at room temperature for 7 hours. The reaction solution was diluted with water, and extracted with ethyl acetate. The organic layer was washed with saturated ammonium chloride (×3), and then dried over anhydrous sodium sulfate and concentrated to give the title compound as a brown oil (13.07 g).

$^1$H-NMR(CDCl$_3$)δ: 3.94 (s, 3H) 5.42 (s, 2H) 7.30-7.49 (m, 7H) 8.29 (dd, J=0.8, 5.2 Hz, 1H)

Production Example 10-c)

[2-(Benzyloxy)-4-pyridyl]methanol

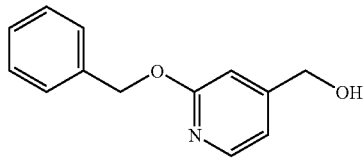

A suspension of lithium aluminum hydride (3.0 g) in diethyl ether (300 mL) was cooled on ice in a nitrogen atmosphere, and then a solution of methyl 2-(benzyloxy) isonicotinate (13.07 g) in diethyl ether (50 mL) wad added dropwise thereinto over 1.5 hours. After stirring for 1 hour, water (3 mL), 5N aqueous sodium hydroxide solution (3 mL) and water (9 mL) were successively added dropwise thereinto under ice-cooling. The insoluble matters were filtered off and washed with diethyl ether, and the filtrate was concentrated. After diethyl ether was added to the residue, the solution was dried over anhydrous sodium sulfate and then concentrated. The residue was purified by silica gel column chromatography to give the title compound as a pale red oil (9.57 g).

$^1$H-NMR(CDCl$_3$)δ: 1.97 (br s, 1H) 4.68 (s, 2H) 5.38 (s, 2H) 6.82 (s, 1H) 6.86-6.89 (m, 1H) 7.29-7.41 (m, 3H) 7.43-7.48 (m, 2H) 8.13 (d, J=5.2 Hz, 1H)

Production Example 10-d)

2-(Benzyloxy)isonicotinaldehyde

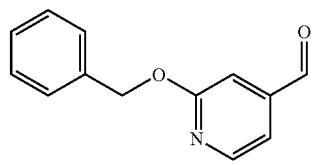

A suspension of [2-(benzyloxy)-4-pyridyl]methanol (6.0 g) and activated manganese dioxide (30 g) in chloroform (180 mL) was heated under reflux for 2.5 hours. After the reaction solution was allowed to cool to room temperature, the manganese dioxide was filtered off and washed with ethyl acetate. The filtrate was concentrated to give the title compound as a pale brown oil (5.34 g).

$^1$H-NMR(CDCl$_3$)δ: 5.44 (s, 2H) 7.20-7.22 (m, 1H) 7.30-7.42 (m, 4H) 7.45-7.50 (m, 2H) 8.38 (d, J=5.6 Hz, 1H) 10.01 (s, 1H)

Production Example 10-e)

2-Ethoxy-3-(2-oxo-1,2-dihydro-4-pyridinyl)propanoic acid

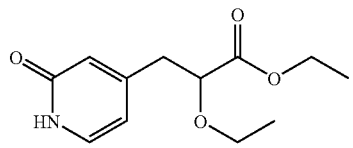

A suspension of sodium hydride (360 mg) in tetrahydrofuran (50 mL) was cooled on ice in a nitrogen atmosphere, and ethyl 2-(diethoxyphosphoryl)-2-ethoxyacetate (8.0 g) was added dropwise thereinto over 5 minutes. After stirring as it was for 15 minutes, a solution of 2-(benzyloxy) isonicotinaldehyde (1.74 g) in N,N-dimethylformamide (10 mL) was added dropwise thereinto. After stirring at room temperature for 13.5 hours, the reaction solution was diluted with ethyl acetate and saturated aqueous ammonium chloride solution. The organic layer was washed with saturated aqueous ammonium chloride solution (×2), dried over anhydrous sodium sulfate and then concentrated. The residue was purified by silica gel column chromatography to give propenoic acid derivative (2.74 g; the total weight of the cis form and the trans form). This product was dissolved in methanol (60 mL), added with 10% palladium carbon (280 mg), and stirred at room temperature for 2 hours in a hydrogen atmosphere. The catalyst was filtered off and washed with ethyl acetate. The filtrate was evaporated to give the title compound as a pale yellow oil (1.87 g).

$^1$H-NMR(CDCl$_3$)δ: 1.19 (t, J=7.2 Hz, 3H) 1.19 (t, J=7.2 Hz, 3H) 2.82-2.92 (m, 2H) 3.39 (dq, J=7.2, 9.2 Hz, 1H) 3.66 (dq, J=7.2, 9.2 Hz, 1H) 4.03 (dd, J=4.8, 8.0 Hz, 1H) 4.18-4.26 (m, 2H) 6.25 (dd, J=1.6, 6.6 Hz, 1H) 6.45 (dd, J=0.6, 1.6 Hz, 1H) 7.29 (dd, J=0.6, 6.6 Hz, 1H) 12.92 (br s, 1H)

Production Example 10-f)

Ethyl 2-isopropoxy-3-(2-oxo-1,2-dihydro-4-pyridinyl)propanoate

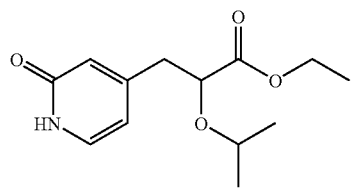

The compound of Production Example 10-f) was synthesized in the same manner as in Production Example 10-e), except that 2-(diethoxyphosphoryl)-2-isopropoxyacetate was used.

$^1$H-NMR(CDCl$_3$)δ: 1.03 (d, J=6.0 Hz, 3H) 1.18 (d, J=6.0 Hz, 3H) 1.29 (t, J=7.2 Hz, 3H) 2.80 (dd, J=8.8,14.0 Hz, 1H) 2.87 (dd, J=4.0,14.0 Hz, 1H) 3.58 (sept, J=6.0 Hz, 1H) 4.08 (dd, J=4.0, 8.8 Hz, 1H) 4.18-4.27 (m, 2H) 6.26 (dd, J=1.6, 6.4 Hz, 1H) 6.46 (d, J=1.6 Hz, 1H) 7.30 (d, J=6.4 Hz, 1H)

Production Example 10-g)

Ethyl 3-{1-[2-(2,4-dichlorophenoxy)ethyl]-2-oxo-1,2-dihydro-4-pyridinyl}-2-isopropoxypropanoate and 10-h): ethyl 3-{2-[2-(2,4-dichlorophenoxy)ethoxy]-4-pyridyl}-2-isopropoxypropanoate

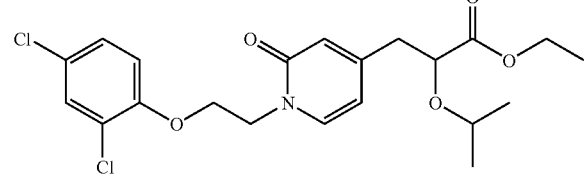

and

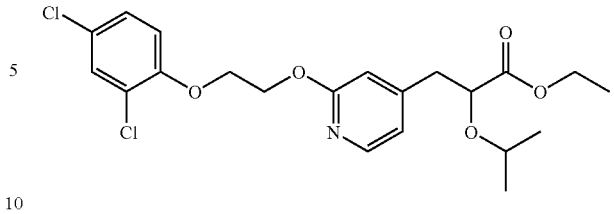

A suspension of sodium hydride (16 mg) in N,N-dimethylformamide (1 mL) was cooled on ice in a nitrogen atmosphere, and a solution of ethyl 2-isopropoxy-3-(2-oxo-1,2-dihydro-4-pyridinyl)propanoate (100 mg) in N,N-dimethylformamide (1 mL) and a solution of 1-(2-bromoethoxy)-2,4-dichlorobenzene (120 mg) in N,N-dimethylformamide (1 mL) were successively added thereto. After stirring the mixture for 3.5 hours, saturated aqueous ammonium chloride solution and ethyl acetate were added thereto. The organic layer was washed with saturated aqueous ammonium chloride solution, saturated aqueous sodium hydrogencarbonate solution and saturated aqueous ammonium chloride solution successively, dried over anhydrous sodium sulfate and concentrated. The residue was purified on a preparative TLC plate to give the individual title compounds.

Ethyl 3-{1-[2-(2,4-dichlorophenoxy)ethyl]-2-oxo-1,2-dihydro-4-pyridinyl}-2-isopropoxypropanoate (Production Example 10-g)) (76 mg, colorless oil):

$^1$H-NMR(CDCl$_3$)δ: 0.97 (d, J=6.0 Hz, 3H) 1.14 (d, J=6.0 Hz, 3H) 1.24 (t, J=7.2 Hz, 3H) 2.71-2.83 (m, 2H) 3.54 (sept, J=6.0 Hz, 1H) 4.04 (dd, J=4.4, 8.4 Hz, 1H) 4.13-4.22 (m, 2H) 4.27 (t, J=4.4 Hz, 2H) 4.34 (t, J=4.4 Hz, 2H) 6.17 (dd, J=1.6, 6.8 Hz, 1H) 6.43 (d, J=1.6 Hz, 1H) 6.77 (d, J=9.0 Hz, 1H) 7.14 (dd, J=2.6, 9.0 Hz, 1H) 7.31 (d, J=2.6 Hz, 1H) 7.44 (d, J=6.8 Hz, 1H)

Ethyl 3-{2-[2-(2,4-dichlorophenoxy)ethoxy]-4-pyridyl}-2-isopropoxypropanoate (Production Example 10-h)) (24 mg, pale yellow oil):

$^1$H-NMR(CDCl$_3$)δ: 0.97 (d, J=6.0 Hz, 3H) 1.15 (d, J=6.0 Hz, 3H) 1.25 (t, J=7.2 Hz, 3H) 2.85-2.97 (m, 2H) 3.52 (sept, J=6.0 Hz, 1H) 4.06 (dd, J=4.6,8.6 Hz, 1H) 4.14-4.25 (m, 2H) 4.35 (t, J=4.8 Hz, 2H) 4.68 (t, J=4.8 Hz, 2H) 6.68 (d, J=1.6 Hz, 1H) 6.81 (dd, J=1.6,5.2 Hz, 1H) 6.93 (d, J=8.8 Hz, 1H) 7.17 (dd, J=2.4,8.8 Hz, 1H) 7.35 (d, J=2.4 Hz, 1H) 8.30 (d, J=5.2 Hz, 1H)

Example 1

3-{2-[2-(2,4-Dichlorophenoxy)ethoxy]-4-pyridyl}-2-isopropoxypropanoic acid

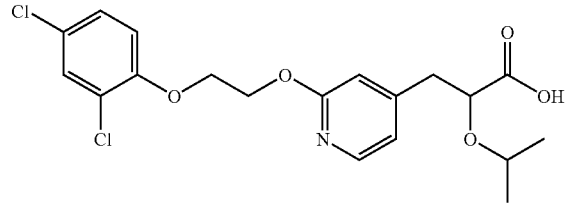

To a suspension of ethyl 3-{2-[2-(2,4-dichlorophenoxy)ethoxy]-4-pyridyl}-2-isopropoxypropanoate (24 mg) in methanol (2 mL) was added 5N aqueous sodium hydroxide solution (0.4 mL), and the resulting solution was stirred at room temperature for 12 hours. The reaction solution was diluted with water, and adjusted to pH 5 with 5N hydrochloric acid. After extracting with ethyl acetate (×2), and the combined organic layers were dried over anhydrous sodium sulfate and concentrated. The residue was purified on a preparative TLC plate to give the title compound as a colorless solid (16 mg).

$^1$H-NMR(CDCl$_3$)δ: 1.02 (d, J=6.0 Hz, 3H) 1.16 (d, J=6.0 Hz, 3H) 2.90 (dd, J=8.2,13.8 Hz, 1H) 3.04 (dd, 3.4,13.8 Hz, 1H) 3.57 (sept, J=6.0 Hz, 1H) 4.13 (dd, J=3.4,8.2 Hz, 1H) 4.35 (t, J=4.8 Hz, 2H) 4.68 (t, J=4.8 Hz, 2H) 6.69 (br s, 1H) 6.82 (dd, J=0.8,5.2 Hz, 1H) 6.92 (d, J=8.8 Hz, 1H) 7.17 (dd, J=2.6,8.8 Hz, 1H) 7.35 (d, J=2.6 Hz, 1H) 8.05 (d, J=5.2 Hz, 1H)

Example 2

3-{1-[2-(2,4-Dichlorophenoxy)ethyl]-2-oxo-1,2-dihydro-4-pyridinyl}-2-isopropoxypropanoic acid

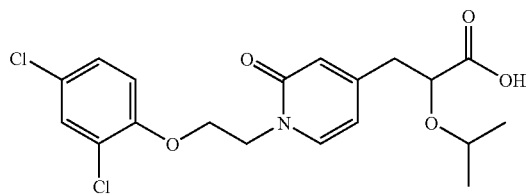

The compound was synthesized in the same manner as in Example 1, except that ethyl 3-{1-[2-(2,4-dichlorophenoxy) ethyl]-2-oxo-1,2-dihydro-4-pyridinyl}-2-isopropoxypropanoate was used.

$^1$H-NMR(CDCl$_3$)δ: 1.06 (d, J=6.0 Hz, 3H) 1.17 (d, J=6.0 Hz, 3H) 2.82-2.94 (m, 2H) 3.65 (sept, J=6.0 Hz, 1H) 4.14 (t, J=6.0 Hz, 1H) 4.27 (t, J=4.4 Hz, 2H) 4.30-4.41 (m, 2H) 6.29 (dd, J=1.2, 6.8 Hz, 1H) 6.57 (br s, 1H) 6.77 (d, J=8.8 Hz, 1H) 7.14 (dd, J=2.4, 8.8 Hz, 1H) 7.31 (d, J=2.4 Hz, 1H) 7.48 (d, J=6.8 Hz, 1H)

Example 3-a)

2-Isopropoxy-3-(2-oxo-1-{2-[4-(trifluoromethyl) phenoxy]ethyl}-1,2-dihydro-4-pyridinyl)propanoic acid and 3-b): 2-isopropoxy-3-(2-{2-[4-(trifluoromethyl)phenoxy]ethoxy}-4-pyridyl)propanoic acid

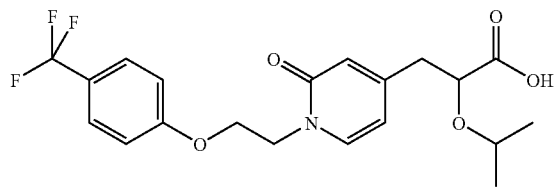

and

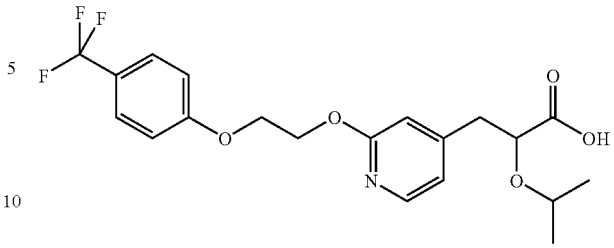

A suspension of ethyl 3-{2-[2-(2,4-dichlorophenoxy) ethoxy]-4-pyridyl}-2-isopropoxypropanoate (20 mg), 1-(2-bromoethoxy)-4-(trifluoromethyl)benzene (30 mg) and potassium carbonate (22 mg) in N,N-dimethylformamide (0.4 mL) was stirred at 70° C. for 13 hours. The reaction solution was diluted with water and extracted with ethyl acetate. After the organic layer was concentrated, the residue was dissolved in ethanol (0.4 mL), added with 5N aqueous sodium hydroxide solution (0.1 mL), and then stirred at room temperature for 1.5 hours. The reaction solution was diluted with water and then neutralized with 5N hydrochloric acid. The resulting solution was extracted with ethyl acetate, and then purified on a reversed phase column using water-acetonitrile-trifluoroacetic acid as the eluting solvent, to give the individual title compounds.

2-Isopropoxy-3-(2-oxo-1-{2-[4-(trifluoromethyl)phenoxy] ethyl}-1,2-dihydro-4-pyridinyl)propanoic acid (Example 3-a)) (11.22 mg):

$^1$H-NMR(CDCl$_3$)δ: 1.08 (d, J=6.0 Hz, 3H) 1.19 (d, J=6.0 Hz, 3H) 2.88 (dd, 6.8, 13.6 Hz, 1H) 2.94 (dd, 5.2, 13.6 Hz, 1H) 3.68 (sept, J=6.0 Hz, 1H) 4.17 (dd, 5.2, 6.8 Hz, 1H) 4.30-4.41 (m, 4H) 6.32 (dd, J=1.6, 6.8 Hz, 1H) 6.63 (d, J=1.6 Hz, 1H) 6.91 (d, J=8.8 Hz, 2H) 7.39 (d, J=6.8 Hz, 1H) 7.52 (d, J=8.8 Hz, 2H)

MS m/e (ESI) 414 (MH$^+$)

2-Isopropoxy-3-(2-{2-[4-(trifluoromethyl)phenoxy] ethoxy}-4-pyridyl)propanoic acid (Example 3-b)) (6.97 mg):

$^1$H-NMR(CDCl$_3$)δ: 1.06 (d, J=6.0 Hz, 3H) 1.18 (d, J=6.0 Hz, 3H) 2.93 (dd, J=8.0, 14.0 Hz, 1H) 3.06 (dd, J=4.0, 14.0 Hz, 1H) 3.60 (sept, J=6.0 Hz, 1H) 4.16 (dd, J=3.4, 8.2 Hz, 1H) 4.36 (t, J=4.8 Hz, 2H) 4.68 (t, J=4.8 Hz, 2H) 6.70 (d, J=1.6 Hz, 1H) 6.82 (dd, J=1.6, 5.2 Hz, 1H) 7.02 (d, J=9.0 Hz, 2H) 7.55 (d, J=9.0 Hz, 2H) 8.07 (d, J=5.2 Hz, 1H)

MS m/e (ESI) 414 (MH$^+$)

The compounds of Examples 4 to 31 below were synthesized in the same manner as in Example 3.

Example 4

3-{1-[2-(4-Cyclohexylphenoxy)ethyl]-2-oxo-1,2-dihydro-4-pyridinyl}-2-isopropoxypropanoic acid

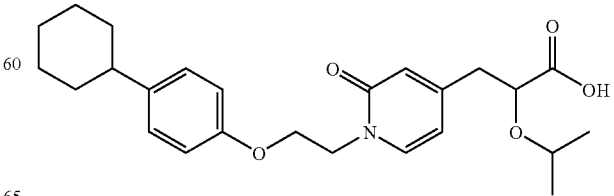

MS m/e (ESI) 428 (MH$^+$)

Example 5

3-{2-[2-(4-Cyclohexylphenoxy)ethoxy]-4-pyridyl}-2-isopropoxypropanoic acid

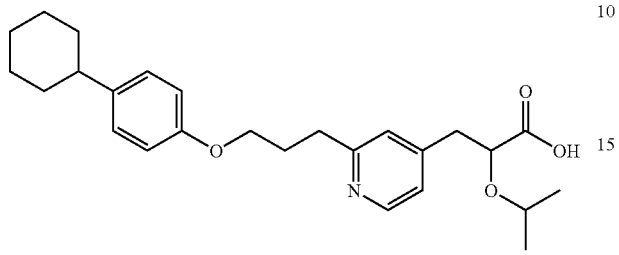

MS m/e (ESI) 428 (MH⁺)

Example 6

3-{1-[2-(4-Cyclopentylphenoxy)ethyl]-2-oxo-1,2-dihydro-4-pyridinyl}-2-isopropoxypropanoic acid

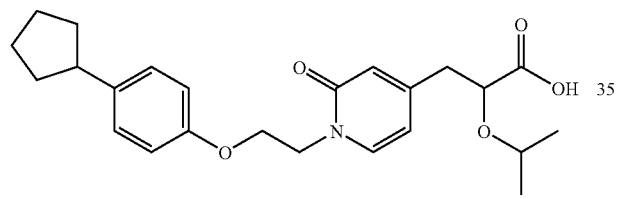

¹H-NMR(CDCl₃)δ: 1.09 (d, J=6.0 Hz, 3H) 1.19 (d, J=6.0 Hz, 3H) 1.45-1.57 (m, 2H) 1.59-1.72 (m, 2H) 1.72-1.83 (m, 2H) 1.97-2.06 (m, 2H) 2.82-2.95 (m, 3H) 3.68 (sept, J=6.0 Hz, 1H) 4.17 (dd, J=5.2,6.8 Hz, 1H) 4.23 (t, J=4.8 Hz, 2H) 4.30 (t, J=4.8 Hz, 2H) 6.24 (dd, J=1.6,7.0 Hz, 1H) 6.55 (d, J=1.6 Hz, 1H) 6.74-6.79 (m, 2H) 7.10-7.15 (m, 2H) 7.39 (d, J=7.0 Hz, 1H)
MS m/e (ESI) 414 (MH⁺)

Example 7

3-{2-[2-(4-Cyclopentylphenoxy)ethoxy]-4-pyridyl}-2-isopropoxypropanoic acid

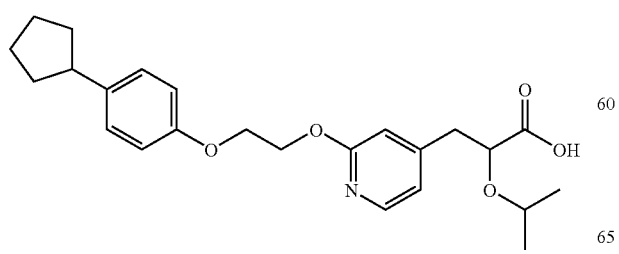

¹H-NMR(CDCl₃)δ: 1.04 (d, J=6.0 Hz, 3H) 1.17 (d, J=6.0 Hz, 3H) 1.48-1.60 (m, 2H) 1.60-1.73 (m, 2H) 1.73-1.84 (m, 2H) 1.98-2.08 (m, 2H) 2.86-2.98 (m, 2H) 3.05 (dd, J=3.8, 14.0 Hz, 1H) 3.58 (sept, J=6.0 Hz, 1H) 4.14 (dd, J=3.8, 8.2 Hz, 1H) 4.30 (t, J=4.8 Hz, 2H) 4.65 (t, J=4.8 Hz, 2H) 6.70 (br s, 1H) 6.80 (dd, J=1.2,5.2 Hz, 1H) 6.86-6.91 (m,2H) 7.13-7.18 (m,2H) 8.06 (d, J=5.2 Hz,1H)
MS m/e (ESI) 414 (MH⁺)

Example 8

3-(1-{2-[4-(tert-butyl)phenoxy)ethyl]-2-oxo-1,2-dihydro-4-pyridinyl}-2-isopropoxypropanoic acid

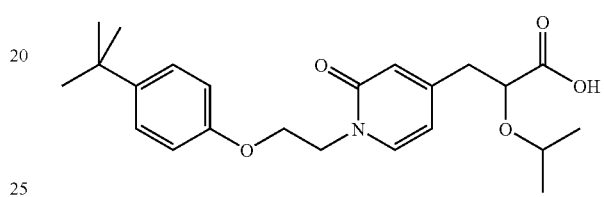

MS m/e (ESI) 402 (MH⁺)

Example 9

3-(2-{2-[4-(tert-butyl)phenoxy)ethoxy]-4-pyridyl}-2-isopropoxypropanoic acid

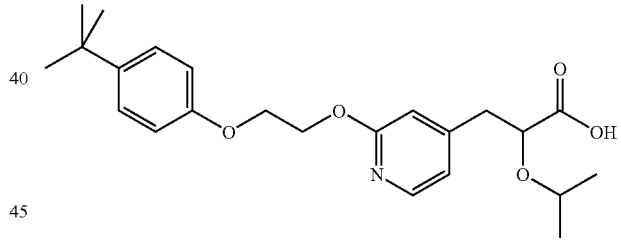

MS m/e (ESI) 402 (MH⁺)

Example 10

2-Isopropoxy-3-{1-[2-(4-isopropylphenoxy)ethyl]-2-oxo-1,2-dihydro-4-pyridinyl}propanoic acid

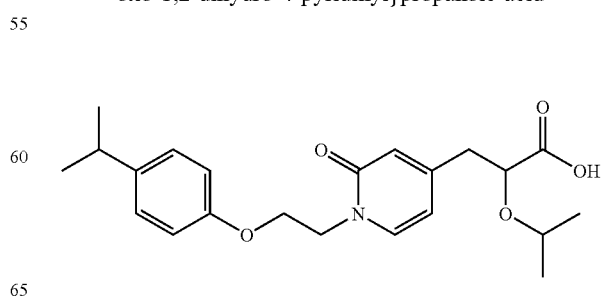

MS m/e (ESI) 388 (MH⁺)

Example 11

2-Isopropoxy-3-{2-[2-(4-isopropylphenoxy)ethoxy]-4-pyridyl}propanoic acid

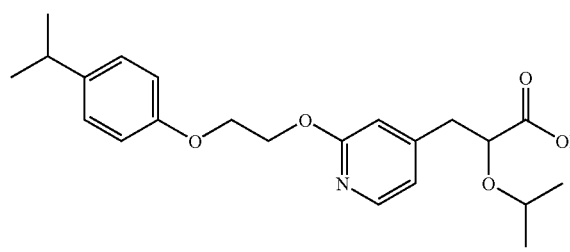

MS m/e (ESI) 388 (MH+)

Example 12

2-Isopropoxy-3-[1-(2-phenoxy)-2-oxo-1,2-dihydro-4-pyridinyl]propanoic acid

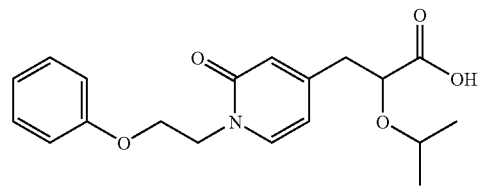

MS m/e (ESI) 346 (MH+)

Example 13

2-Isopropoxy-3-[2-(2-phenoxyethoxy)-4-pyridyl]propanoic acid

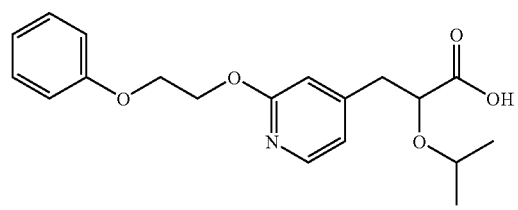

MS m/e (ESI) 346 (MH+)

Example 14

3-{1-[2-(4-Fluorophenoxy)ethyl]-2-oxo-1,2-dihydro-4-pyridinyl)-2-isopropoxypropanoic acid

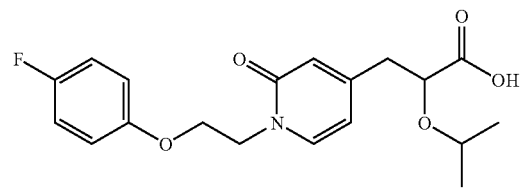

MS m/e (ESI) 364 (MH+)

Example 15

3-{2-[2-(4-Fluorophenoxy)ethoxy]-4-pyridyl}-2-isopropoxypropanoic acid

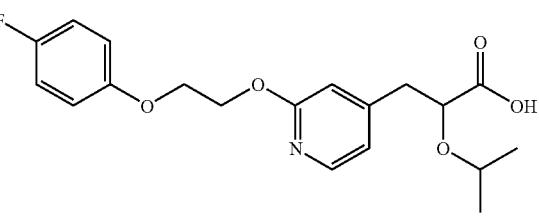

MS m/e (ESI) 364 (MH+)

Example 16

3-{1-[2-(2,4-Dichlorophenoxy)ethyl]-2-oxo-1,2-dihydro-4-pyridinyl}-2-ethoxypropanoic acid

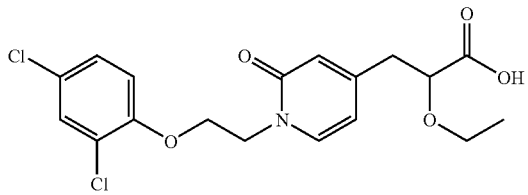

MS m/e (ESI) 400 (MH+)

Example 17

3-{2-[2-(2,4-Dichlorophenoxy)ethoxy]-4-pyridyl}-2-ethoxypropanoic acid

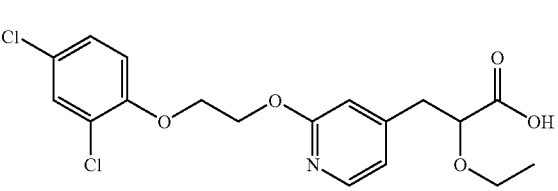

MS m/e (ESI) 400 (MH+)

Example 18

2-Ethoxy-3-(2-oxo-1-{2-[4-(trifluoromethyl)phe-noxy]ethyl}-1,2-dihydro-4-pyridinyl)propanoic acid

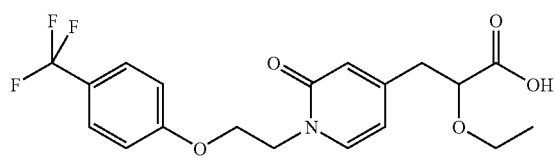

$^1$H-NMR(CDCl$_3$)δ: 1.21 (t, J=7.2 Hz, 3H) 2.91-3.02 (m, 2H) 3.48 (dq, J=7.2, 9.2 Hz, 1H) 3.71 (dq, J=7.2, 9.2 Hz, 1H) 4.13 (t, 6.0 Hz, 1H) 4.27-4.42 (m, 4H) 6.35 (dd, J=1.6, 7.2 Hz, 1H) 6.65 (br s, 1H) 6.91 (d, J=8.4 Hz, 2H) 7.40 (d, J=7.2 Hz, 1H) 7.52 (d, J=8.4 Hz, 2H)

MS m/e (ESI) 400 (MH$^+$)

Example 19

2-Ethoxy-3-(2-{2-[4-(trifluoromethyl)phenoxy]ethoxy}-4-pyridyl)propanoic acid

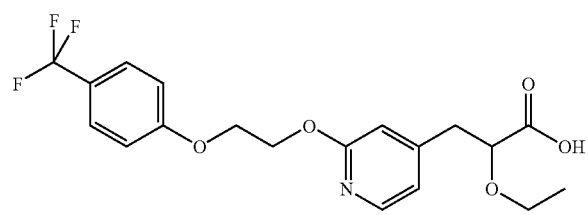

$^1$H-NMR(CDCl$_3$)δ: 1.18 (t, J=7.2 Hz, 3H) 2.96 (dd, J=7.6, 14.0 Hz, 1H) 3.07 (dd, J=4.0, 14.0 Hz, 1H) 3.45 (quint, J=7.2 Hz, 1H) 3.65 (quint, J=7.2 Hz, 1H) 4.09 (dd, J=4.0, 7.6 Hz, 1H) 4.35 (t, J=4.8 Hz, 2H) 4.67 (t, J=4.8 Hz, 2H) 6.70 (br s, 1H) 6.82 (dd, J=1.2, 5.2 Hz, 1H) 7.00 (d, J=8.6 Hz, 2H) 7.54 (d, J=8.6 Hz, 2H) 8.05 (d, J=5.2 Hz, 1H)

MS m/e (ESI) 400 (MH$^+$)

Example 20

3-{1-[2-(4-Cyclohexylphenoxy)ethyl]-2-oxo-1,2-dihydro-4-pyridinyl}-2-ethoxypropanoic acid

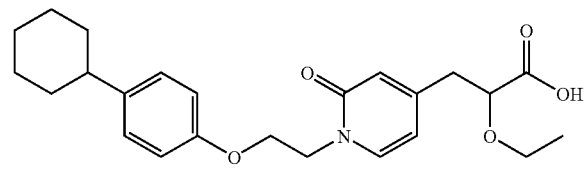

MS m/e (ESI) 414 (MH$^+$)

Example 21

3-[(2-(2-(4-Cyclohexylphenoxy)ethoxy]-4-pyridyl}-2-ethoxypropanoic acid

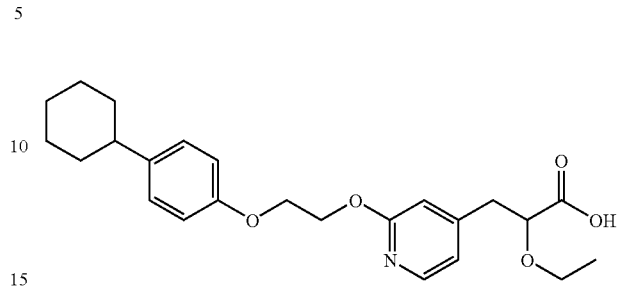

MS m/e (ESI) 414 (MH$^+$)

Example 22

3-{1-[2-(4-Cyclopentylphenoxy)ethyl]-2-oxo-1,2-dihydro-4-pyridinyl}-2-ethoxypropanoic acid

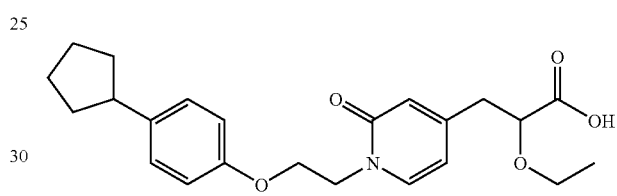

MS m/e (ESI) 400 (MH$^+$)

Example 23

3-{2-[2-(4-Cyclopentylphenoxy)ethoxy]-4-pyridyl}-2-ethoxypropanoic acid

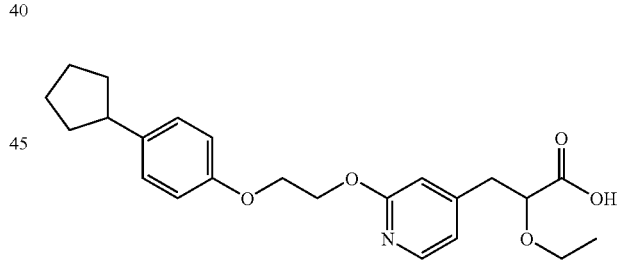

MS m/e (ESI) 400 (MH$^+$)

Example 24

3-(1-{2-[4-(tert-Butyl)phenoxy]ethyl}-2-oxo-1,2-dihydro-4-pyridinyl)-2-ethoxypropanoic acid

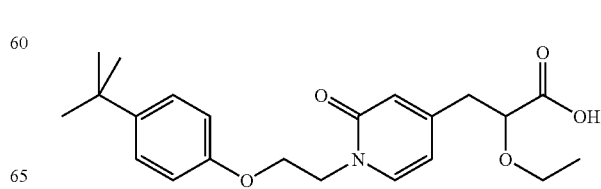

¹H-NMR(CDCl₃)δ: 1.21 (t, J=6.8z, 3H) 1.28 (s, 9H) 2.93 (dd, 6.8, 14.0 Hz, 1H) 3.00 (dd, 4.6, 14.0 Hz, 1H) 3.49 (dq, J=7.2, 9.0 Hz, 1H) 3.70 (dq, J=7.2, 9.0 Hz, 1H) 4.12 (dd, J=4.6, 6.8 Hz, 1H) 4.25 (t, 4.6 Hz, 2H) 4.30-4.42 (m, 2H) 6.37 (dd, J=1.4, 7.0 Hz, 1H) 6.70 (br s, 1H) 6.75-6.81 (m, 2H) 7.25-7.30 (m, 2H) 7.47 (d, J=7.0 Hz, 1H)

MS m/e (ESI) 388 (MH⁺)

Example 25

3-(2-{2-[4-(tert-Butyl)phenoxy]ethoxy}-4-pyridyl)-2-ethoxypropanoic acid

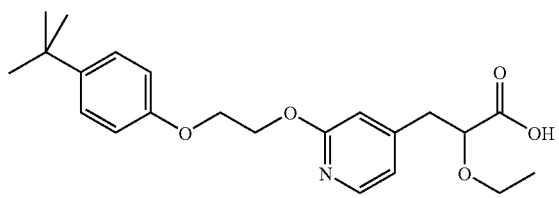

¹H-NMR(CDCl₃)δ: 1.19 (t, J=6.8z, 3H) 1.30 (s, 9H) 2.96 (dd, 7.6, 14.0 Hz, 1H) 3.08 (dd, 4.0, 14.0 Hz, 1H) 3.50 (quint, J=6.8 Hz, 1H) 3.62 (quint, J=6.8 Hz, 1H) 4.11 (dd, J=4.0, 7.6 Hz, 1H) 4.31 (t, J=4.8 Hz, 2H) 4.65 (t, J=4.8 Hz, 2H) 6.70 (br s, 1H) 6.80 (d, J=5.2 Hz, 1H) 6.87-6.92 (m, 2H) 7.28-7.33 (m, 2H) 8.06 (d, J=5.2 Hz, 1H)

MS m/e (ESI) 388 (MH⁺)

Example 26

2-Ethoxy-3-{1-[2-(4-isopropylphenoxy)ethyl]-2-oxo-1,2-dihydro-4-pyridinyl}propanoic acid

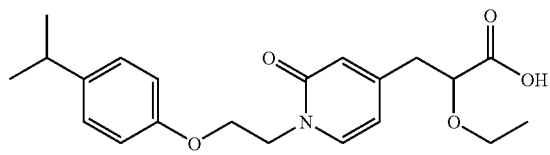

¹H-NMR(CDCl₃)δ: 1.14-1.28 (m, 9H) 2.84 (sept, J=7.2 Hz, 1H) 2.93 (dd, 6.8, 14.0 Hz, 1H) 3.00 (dd, 4.8, 14.0 Hz, 1H) 3.49 (dq, J=7.2, 9.2 Hz, 1H) 3.69 (dq, J=7.2, 9.2 Hz, 1H) 4.09-4.15 (m, 1H) 4.25 (t, 4.0 Hz, 2H) 4.30-4.41 (m, 2H) 6.37 (dd, J=1.4, 6.8 Hz, 1H) 6.70 (br s, 1H) 6.77 (d, J=8.6 Hz, 2H) 7.12 (d, J=8.6 Hz, 2H) 7.47 (d, J=6.8 Hz, 1H)

MS m/e (ESI) 374 (MH⁺)

Example 27

2-Ethoxy-3-{2-[2-(4-isopropylphenoxy)ethoxy]-4-pyridyl}propanoic acid

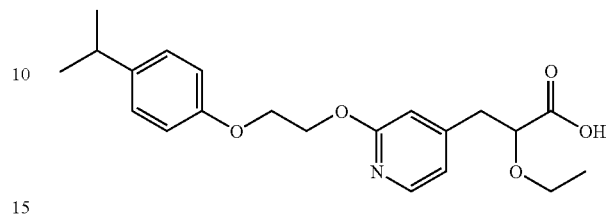

¹H-NMR(CDCl₃)δ: 1.19 (t, J=7.2 Hz, 3H) 1.22 (d, J=7.2 Hz, 6H) 2.86 (sept, J=7.2 Hz, 1H) 2.95 (dd, 8.0, 14.0 Hz, 1H) 3.08 (dd, 4.0, 14.0 Hz, 1H) 3.48 (dq, J=7.2, 9.2 Hz, 1H) 3.63 (dq, J=7.2, 9.2 Hz, 1H) 4.10 (dd, J=4.0, 8.0 Hz, 1H) 4.30 (t, J=4.8 Hz, 2H) 4.65 (t, J=4.8 Hz, 2H) 6.70 (br s, 1H) 6.80 (dd, J=1.2, 5.2 Hz, 1H) 6.86-6.92 (m, 2H) 7.12-7.17 (m, 2H) 8.06 (d, J=5.2 Hz, 1H)

MS m/e (ESI) 374 (MH⁺)

Example 28

2-Ethoxy-3-[1-(2-phenoxy)-2-oxo-1,2-dihydro-4-pyridinyl]propanoic acid

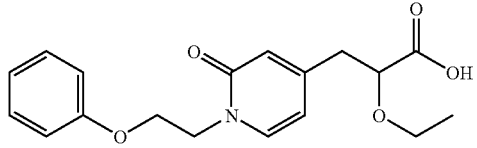

MS m/e (ESI) 332 (MH⁺)

Example 29

2-Ethoxy-3-[2-(2-phenoxyethoxy)-4-pyridinyl]propanoic acid

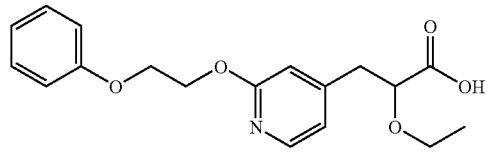

MS m/e (ESI) 332 (MH⁺)

Example 30

2-Ethoxy-3-{1-[2-(4-fluorophenoxy)ethyl]-2-oxo-1,2-dihydro-4-pyridinyl}propanoic acid

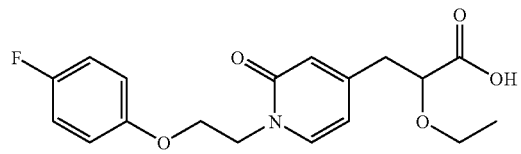

MS m/e (ESI) 350 (MH⁺)

Example 31

2-Ethoxy-3-{2-[2-(4-fluorophenoxy)ethoxy]-4-pyridyl}propanoic acid

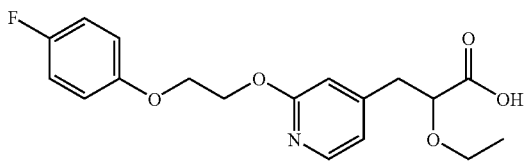

MS m/e (ESI) 350 (MH+)

What is claimed is:

1. A carboxylic acid compound represented by the formula (I), or a salt thereof:

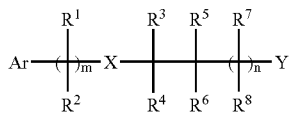

wherein Ar represents a $C_{6-10}$ aryl group optionally having at least one substituent;
$R^1$, $R^2$, $R^3$, $R^4$, $R^5$, $R^6$, $R^7$ and $R^8$ are the same as or different from each other and each represents a hydrogen atom, a hydroxyl group, a halogen atom, a $C_{1-6}$ alkyl group or a $C_{1-6}$ alkoxy group;
X represents an oxygen atom or a methylene group;
Y represents a group represented by the formula (II) or (III):

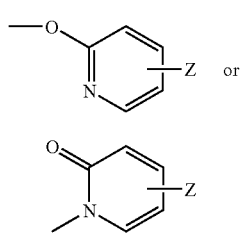

wherein Z represents a group represented by the formula (IV):

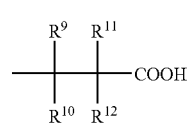

wherein $R^9$, $R^{10}$, $R^{11}$ and $R^{12}$ are the same as or different from each other and each represents a hydrogen atom, a halogen atom, a hydroxyl group, a $C_{1-6}$ alkyl group or a $C_{1-6}$ alkoxy group;
m is 0 or 1; and
n is 0 or 1.

2. The carboxylic acid compound according to claim 1 or a salt thereof, wherein Y is a group represented by the formula (II):

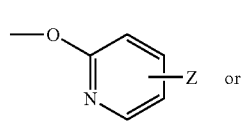

wherein Z represents a group represented by the formula (IV):

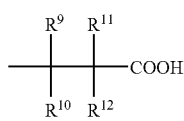

wherein $R^9$, $R^{10}$, $R^{11}$ and $R^{12}$ are independent of each other and each represents a hydrogen atom, a halogen atom, a hydroxyl group, a $C_{1-6}$ alkyl group or a $C_{1-6}$ alkoxy group.

3. The carboxylic acid compound according to claim 1 or a salt thereof, wherein Y represents a group represented by the formula (III):

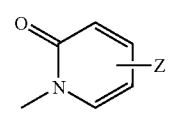

wherein Z represents a group represented by the formula (IV):

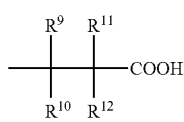

wherein $R^9$, $R^{10}$, $R^{11}$ and $R^{12}$ are independent of each other and each represents a hydrogen atom, a halogen atom, a hydroxyl group, a $C_{1-6}$ alkyl group or a $C_{1-6}$ alkoxy group.

4. The carboxylic acid compound according to claim 1 or a salt thereof, wherein each of $R^9$, $R^{10}$ and $R^{11}$ represents a hydrogen atom; and $R^{12}$ represents a $C_{1-6}$ alkoxy group.

5. The carboxylic acid compound according to claim 1 or a salt thereof, wherein $R^{12}$ represents an ethoxy group or an isopropoxy group.

6. The carboxylic acid compound according to claim 1 or a salt thereof, wherein X represents an oxygen atom.

7. The carboxylic acid compound according to claim 1 or a salt thereof, wherein each of m and n represents 0.

8. The carboxylic acid compound according to claim 1 or a salt thereof, wherein each of $R^1$, $R^2$, $R^3$, $R^4$, $R^5$, $R^6$, $R^7$ and $R^8$ represents a hydrogen atom.

9. The carboxylic acid compound according to claim 1 or a salt thereof, wherein Ar represents a benzene ring group optionally having at least one substituent selected from the group consisting of a halogen atom, a hydroxyl group, a $C_{1-6}$ alkyl group, a $C_{1-6}$ alkoxy group, a $C_{3-6}$ cycloalkyl group and a trifluoromethyl group.

10. A method for treating diabetes mellitus, syndrome X or an inflammatory disease, said method comprising administering a pharmacologically effective amount of the carboxylic acid compound according to claim 1 or a salt thereof to a patient in need thereof.

11. The carboxylic acid compound according to claim 1 or a salt thereof, wherein said at least one substituent of said Ar is selected from the group comprising an alkyl group, alkenyl group, alkynyl group and alkoxy group, wherein any of said groups is further optionally substituted with a hydroxyl group, thiol group, nitro group, morpholino group, thiomorpholino group, a halogen atom, nitrile group, azide group, formyl group, amino group, an alkylamino group, a dialkylamino group, carbamoyl group or sulfonyl group.

12. The carboxylic acid compound according to claim 1 or a salt thereof, wherein said at least one substituent of said Ar is selected from the group comprising a halogen atom, hydroxy group, $C_{1-6}$ alkyl group, halogenated $C_{1-6}$ alkyl group, $C_{3-6}$ cycloalkyl group arid a $C_{1-6}$ alkoxy group.

13. A pharmaceutical composition comprising:
   a pharmacologically effective amount of the compound according to claim 1 or a salt thereof; and
   a pharmaceutically acceptable carrier.

14. The method of claim 10, wherein said inflammatory disease is an inflammatory bowel disease.

15. The method of claim 10, wherein said disease is diabetes mellitus or syndrome X.

* * * * *